US009833312B2

(12) United States Patent
Galstian et al.

(10) Patent No.: US 9,833,312 B2
(45) Date of Patent: Dec. 5, 2017

(54) LIQUID CRYSTAL OPTICAL DEVICE WITH ADVANCED ELECTRIC FIELD CONTROL CAPABILITY

(71) Applicant: LENSVECTOR INC., Sunnyvale, CA (US)

(72) Inventors: Tigran Galstian, Quebec (CA); Karen Asatryan, Quebec (CA); Vladimir Presniakov, Quebec (CA); Aram Bagramyan, Quebec (CA); Amir Tork, Quebec (CA); Armen Zohrabyan, Quebec (CA); Simon Careau, Quebec (CA)

(73) Assignee: LENSVECTOR INC., Sunnyvale, CA (US)

( * ) Notice: Subject to any disclaimer, the term of this patent is extended or adjusted under 35 U.S.C. 154(b) by 0 days.

(21) Appl. No.: 14/653,574

(22) PCT Filed: Dec. 18, 2013

(86) PCT No.: PCT/CA2013/050988
§ 371 (c)(1),
(2) Date: Jun. 18, 2015

(87) PCT Pub. No.: WO2014/094165
PCT Pub. Date: Jun. 26, 2014

(65) Prior Publication Data
US 2016/0000557 A1    Jan. 7, 2016

Related U.S. Application Data

(60) Provisional application No. 61/738,533, filed on Dec. 18, 2012.

(51) Int. Cl.
*A61F 2/16*    (2006.01)
*G02F 1/1343*    (2006.01)
(Continued)

(52) U.S. Cl.
CPC .............. *A61F 2/1627* (2013.01); *A61F 2/16* (2013.01); *G02B 1/16* (2015.01); *G02B 13/0075* (2013.01);
(Continued)

(58) Field of Classification Search
CPC .................. A61F 2/1627; A61F 2/1637; A61F 2210/0076; A61F 2250/0001;
(Continued)

(56) References Cited

U.S. PATENT DOCUMENTS 7,911,526 B2    3/2011    Kageyama
8,896,772 B2 *  11/2014   Fraval .................... G02B 27/22
                                               349/15
(Continued)

FOREIGN PATENT DOCUMENTS

CN    1837864 A    9/2006
CN    101331417 A    12/2008
(Continued)

OTHER PUBLICATIONS

Naumov et al, "Liquid-Crystal Adaptive Lenses with Modal Control", vol. 23, No. 13, (Jul. 1998), pp. 992-994.*
(Continued)

*Primary Examiner* — Paul Prebilic
(74) *Attorney, Agent, or Firm* — Arent Fox LLP

(57) ABSTRACT

A liquid crystal optical device is provided, including a layered structure including at least two support substrates. An external hole patterned control electrode is provided on one of the substrates and has an aperture. An internal hole patterned control electrode is provided on one of the substrates within the aperture, the internal and outer control electrodes being separated by a gap, which forms part of the aperture. A weakly conductive material is provided on one of the substrates over the aperture. A planar transparent
(Continued)

electrode is provided on another one of the substrates. An alignment surface is provided on the substrates over the electrodes. A layer of liquid crystal material is contained by the substrates and in contact with the alignment surface of the substrates. A floating transparent electrode is provided on a side of one of the substrates opposite the outer and the internal hole patterned electrode.

20 Claims, 36 Drawing Sheets

(51) Int. Cl.
    *G02B 13/00*     (2006.01)
    *G02F 1/29*     (2006.01)
    *G02F 1/1337*     (2006.01)
    *G02B 1/16*     (2015.01)

(52) U.S. Cl.
    CPC ........ *G02F 1/1337* (2013.01); *G02F 1/13439* (2013.01); *G02F 1/134309* (2013.01); *G02F 1/29* (2013.01)

(58) Field of Classification Search
    CPC ..... A61F 2250/0004; A61F 2250/0091; G02F 1/13439; G02F 1/29; G02F 1/1337; G02F 1/13306; G02F 1/134309; G02F 2201/05; G02F 2201/06; G02F 2201/12–2201/122; G02F 2202/10; G02F 2203/01; G02F 2203/06; G02F 2203/09; G02F 2203/18
    See application file for complete search history.

(56) References Cited

U.S. PATENT DOCUMENTS

| | | | |
|---|---|---|---|
| 2006/0215107 A1 | 9/2006 | Horiuchi et al. | |
| 2006/0273284 A1* | 12/2006 | Hirose | G02B 3/14 252/299.61 |
| 2008/0055713 A1 | 3/2008 | Ogasawara et al. | |
| 2008/0208335 A1* | 8/2008 | Blum | A61F 2/1616 623/6.22 |
| 2012/0113318 A1 | 5/2012 | Galstian et al. | |
| 2012/0188490 A1 | 7/2012 | Zohrabyan et al. | |
| 2012/0257131 A1 | 10/2012 | Galstian et al. | |

FOREIGN PATENT DOCUMENTS

| | | | | |
|---|---|---|---|---|
| CN | 102812393 A | | 12/2012 | |
| WO | WO 2009/153764 | * | 12/2009 | ................ C08J 3/28 |
| WO | WO 2012/048431 | * | 4/2012 | ............. G02F 1/137 |

OTHER PUBLICATIONS

International Search Report dated Mar. 5, 2014, in corresponding International Patent Application No. PCT/CA2013/050988.
Chinese Office Action of related Chinese Patent Application No. 201380073130.1 dated Jul. 25, 2017.

* cited by examiner

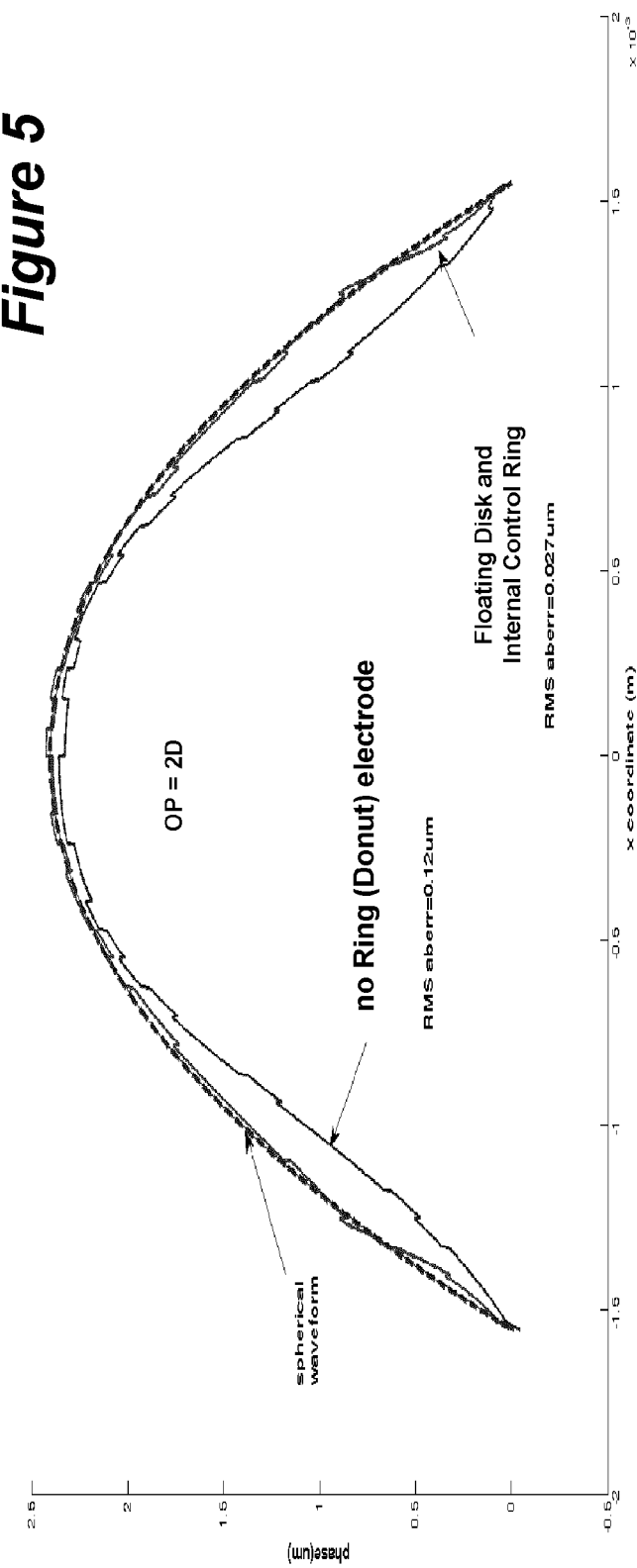

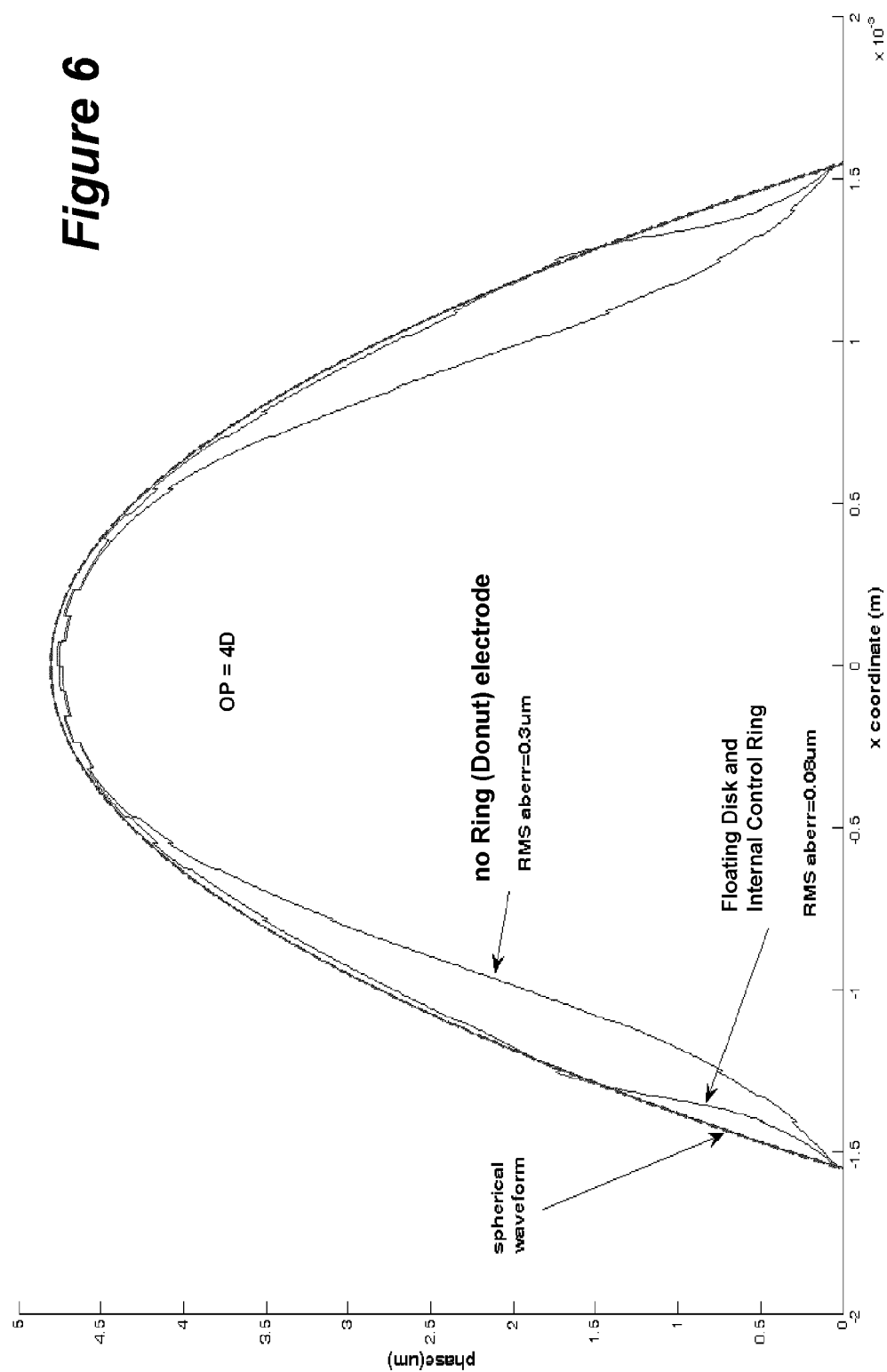

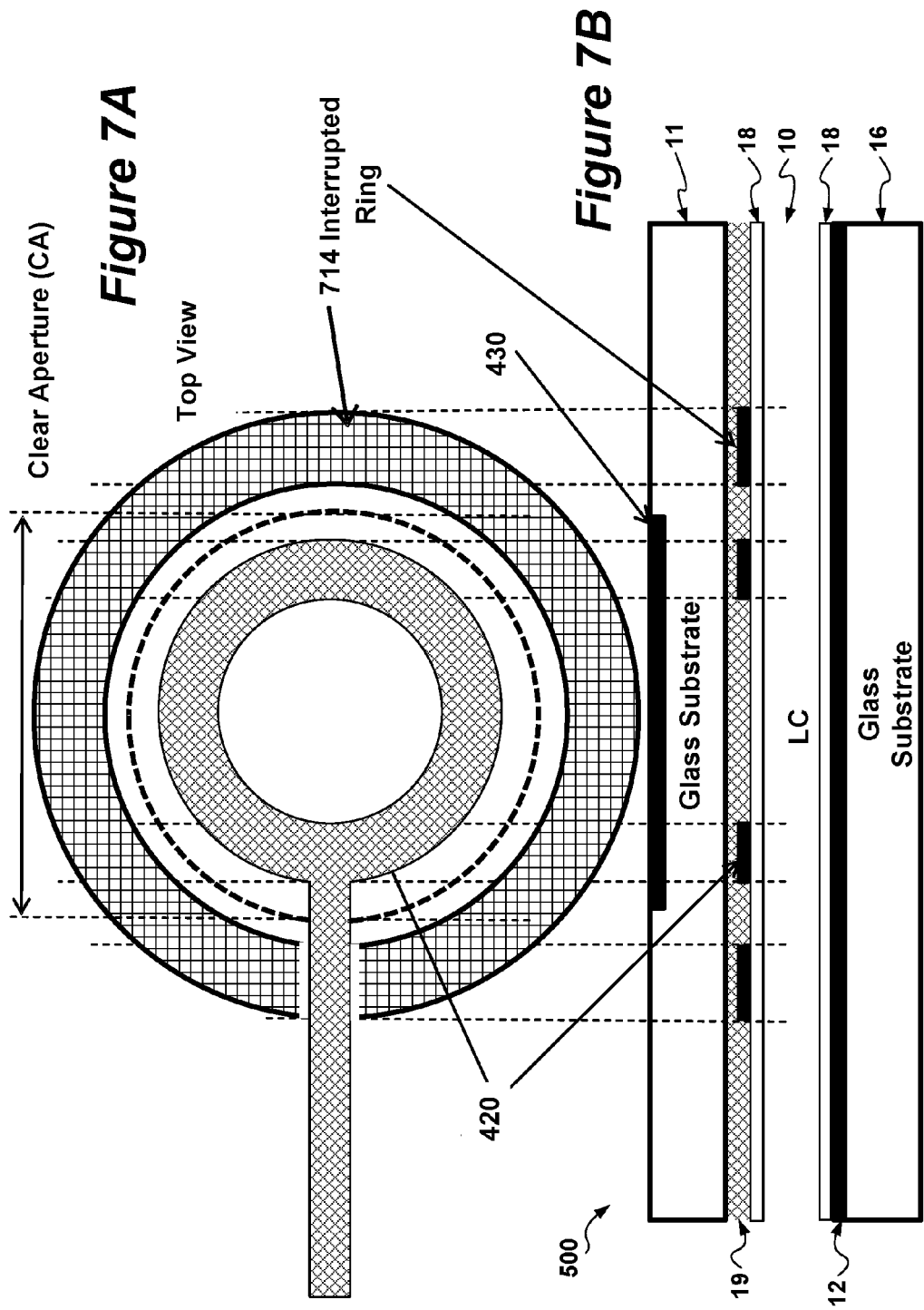

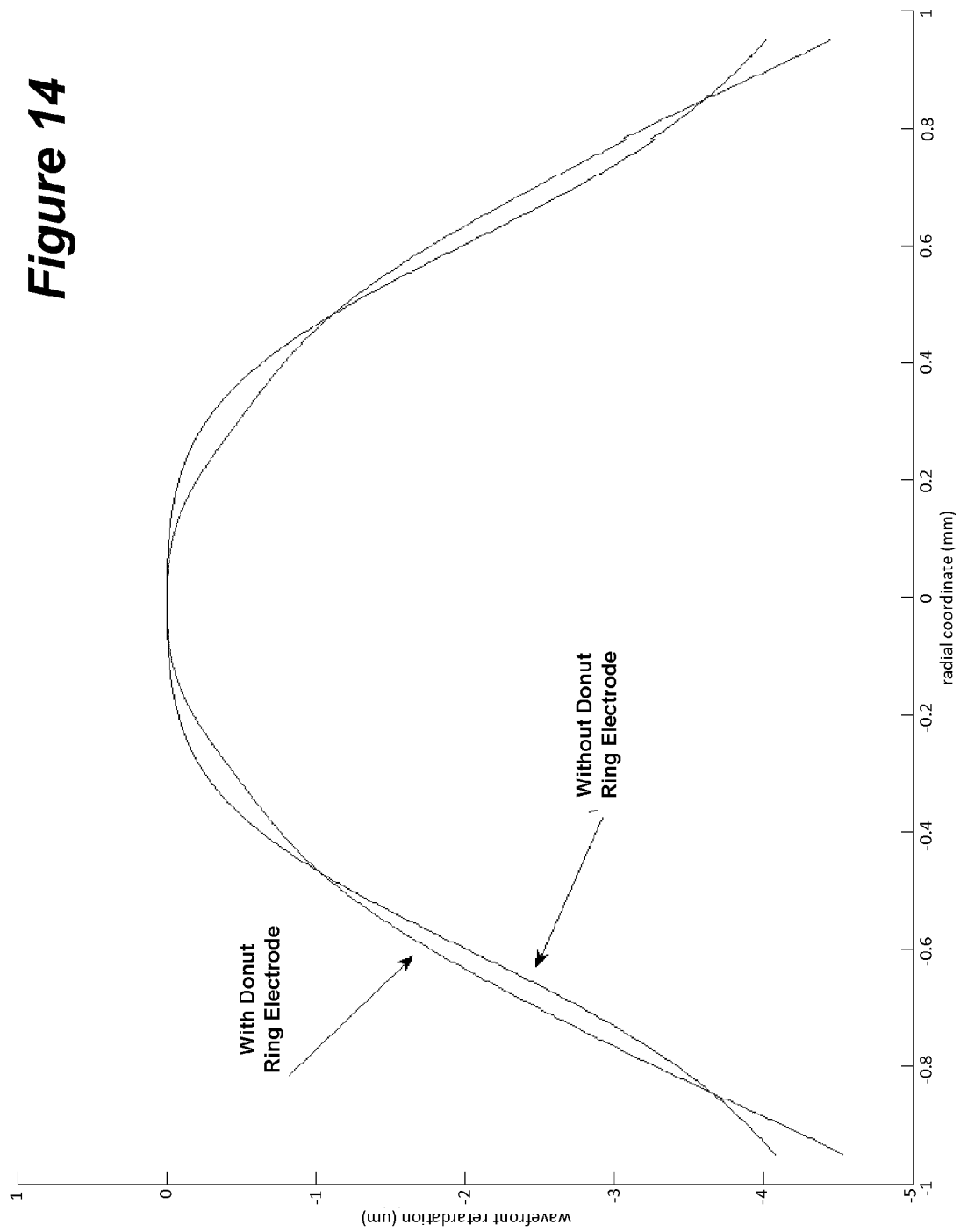

LIQUID CRYSTAL OPTICAL DEVICE WITH ADVANCED ELECTRIC FIELD CONTROL CAPABILITY

CROSS-REFERENCE TO RELATED APPLICATIONS

This application is a 371 National Stage application claiming priority from International PCT Patent Application PCT/CA2013/050988, filed Dec. 18, 2013; and is a non-provisional of, which claims priority from U.S. Provisional Patent Application 61/738,533 filed Dec. 18, 2012, both of which are incorporated herein by reference in their entireties.

TECHNICAL FIELD

The present invention relates to liquid crystal optical devices and in particular to their control electrodes.

BACKGROUND

Liquid Crystal (LC) lenses, and a few other liquid crystal optical devices, are known in the art. One LC lens geometry has a planar construction in which liquid crystal material is held in a cell between glass or plastic plates. Usable optical lens power can be achieved within a relatively small LC cell thickness.

A variety of liquid crystal optical device designs have been proposed in which the orientation of the LC molecules changes in response to an applied electric field.

It has been shown that a circular hole patterned electrode placed at a distance above a LC layer, under which a uniform planar transparent electrode is located, can provide a LC lens by spatially modulating the electric field acting on such a LC layer. A GRIN lens can be created by controlling relative orientation of LC molecules creating a spatial variation of the index of refraction of the LC material within an aperture of the device.

In an article published by A. F. Naumov et al., entitled "Liquid-Crystal Adaptive Lenses with Modal Control", OPTICS LETTERS/Vol. 23, No. 13/Jul. 1, 1998, a lens such as that shown in FIG. 1 uses an LC layer 10 positioned between a hole patterned electrode 14 located adjacent to a top glass support substrate 11, and a planar, optically transparent, electrode 12 of Indium Tin Oxide (ITO) located adjacent to a bottom glass support substrate 16. Liquid crystal alignment layers 18 are located to either side of the LC layer 10. The principle of operation of the LC lens of FIG. 1 relies on attenuating an electrical potential, and on a corresponding drop in electric field strength in the LC layer (across the hole patterned electrode aperture) between the periphery of the lens where the hole patterned electrode 14 is located, and the center of the lens. Since the typical thickness of LC layer 10 is about 0.05 mm, and typical optical apertures of interest are about 2 mm, i.e. forty times larger, left unaddressed, the radial drop in electric field strength across the LC layer 10 is drastic (rapid). A high resistivity layer 19 is deposited in the central part of the hole patterned electrode 14 to "soften" the drop in electric field strength by taking advantage of electrical signal attenuation provided by a distributed RC circuitry formed by the high resistivity layer 19 and the rest of the optical device layered structure. The resistance is provided mainly by the high resistivity layer 19 and the capacitance is provided mainly by the LC layer 10.

The GRIN lens of FIG. 1 is known to have some useful properties, but suffers from significant drawbacks. In particular, the operation of the lens is extremely sensitive to geometrical and material parameters of the layered structure. The most important of these is the sheet resistance $R_s$ of the high resistivity layer 19, which is defined by $R_s=(d\sigma)^{-1}$, where d is the thickness of the high resistivity layer 19 and σ is its conductivity. This sensitivity complicates greatly the fabrication of a polarization independent Tunable Liquid Crystal Lens (TLCL) based on this technology:

The LC is a birefringent material. Incident light passing through the LC layer may be structured into two orthogonal light polarizations. The single LC lens layer 10 of FIG. 1 focuses a single polarization of light and leaving the other polarization essentially unaffected, therefore as the prior art lens uses a single LC layer 10, the overall LC lens optical device is polarization dependent. For this reason the general single LC layer geometry of FIG. 1 is generically referred to as a half LC lens.

Natural light (incoming from the sun or a lamp) contains a chaotic mixture of polarizations (which may be structured as a sum of two orthogonal polarizations). To provide a full polarization independent LC lens, one approach uses a combination of two half LC lenses, each having mutually orthogonal LC molecular orientation planes.

Two planar half LC lenses, each acting on a different light polarization, are arranged with the intent that each half lens focuses light of a corresponding polarity onto a common focal plane. In practice however, the ability to create different "polarization" LC lenses having identical optical properties is a great challenge. A full LC lens geometry that is too thick, with a large spacing between the two LC layers, results in a large spacing between focal planes of different polarization components and fails to create a clear natural light image due to each light polarization component being focused in different way with respect to a single plane optical sensor. In addition, when the lens shape and/or optical power of the two half LC lenses are not identical, the effect of each half LC lens is different even if the LC layers are positioned relatively close to each other. This difference may arise because of differences in LC layer thicknesses or differences in the sheet resistance values for the two high resistivity layers of the component half LC lenses which are combined to provide polarization independent operation.

The reduced camera sizes for mobile applications impose very difficult and strict requirements on camera design and lens performance. Accordingly, lens design must be carefully optimized taking into account both size and manufacturing cost considerations. In wafer-scale manufacturing, a wafer is produced containing a large number of half LC cells, and two such wafers are bonded together to make wafer level polarization independent full LC optical devices. However, for such separately wafer fabricated half LC lenses to have an identical optical power and lens shape when the two wafers are bonded to each other, the two wafers must have the same properties. While the thicknesses of the LC layers may be somewhat controlled by spacers, control of the sheet resistance of the high resistivity layer is a much more difficult task:

FIG. 2 illustrates one solution 200 proposed in PCT Patent Application WO/2009/153764, which is incorporated herein by reference, and which describes two orthogonally oriented LC layers 210a and 210b to focus orthogonal polarizations of light, arranged, respectively, above and below a common electric field control structure 326 having at least one middle ring hole patterned electrode 214(a, b) which is coated by a high resistivity material 219(a, b). Using a single (not shown) middle hole patterned electrode 214 provides a spatially modulated electric field for both the upper LC layer 210b and the lower LC layer 210a, with each of the two LC layers acting on a different polarization orientation of incident light. It was shown that the two LC lenses in such a geometry, image natural light in a substantially similar way onto the same imaging plane for example that of an image sensor. The spatial profile of the electric fields, and thus the optical power and aberrations, were shown to be essentially the same for both the upper 210b and lower 210a LC layers. In manufacturing, the bottom LC layer 210a has the hole patterned electrode 214a placed on top, and the top LC layer 210b is either fabricated on top (of the middle electrode structure 326) or separately fabricated (as illustrated in dashed line) and then bonded to the bottom LC layer 210a and hole patterned electrode 214a combination. Other 2xx series layers illustrated in FIG. 2 correspond to similar layers in FIG. 1 as described hereinabove, top half LC lens layers appearing in mirror fashion with respect to the bottom half LC lens. While not shown, each LC layer 210a and 210b is located between two liquid crystal alignment layers (see 18 in FIG. 1). Optically transparent conductive layers 212a and 212b are located between an alignment layer and a corresponding (support) substrate 216a and 216b.

Using a hole patterned electrode 214, which employs a highly resistive layer (219a, 219b) of material, placed near the aperture, the electrical sheet resistance $R_s$ of the material plays an important role in defining the shape of the electrical field and lensing properties, and such resistive properties are very important for precise control of the shape of the electric field inside LC layers (200). Controlling the resistance of a thin layer of a semiconductor material (219a, 219b) on a wafer within a required range for lensing operation using a 2 mm clear aperture is a challenge.

In addition, applications such as bar code reading, require auto-focus capability which means that an (electrically or otherwise) variable lens must be used to change the optical power of the overall camera. Such variable optical devices are referred to as Tunable LC Lenses (TLCL). This auto-focus capability destabilizes lens design optimizations introducing a degradation of a modulation transfer function (the transformation of an input optical image to an output optical image) which may be very severe (unacceptable).

SUMMARY

It is realized that in a LC lens wavefronts are typically affected, in a limited way, in monotonic fashion from the center to the periphery of the aperture of the LC optical device. With reference to the solid line in FIG. 3, wavefronts typically generated by hole patterned electrodes have a flattened top and a Gaussian drop-off towards the periphery of the optical device aperture. Depending on material properties of the LC lens and geometry parameters such as: the ratio between the hole patterned electrode diameter, electrode spacing, thicknesses of intermediary layers, etc., the Modulation Transfer Function (MTF) of the LC lens in some cases provides only a central in-focus region within a clear aperture or in other cases only a peripheral in-focus region within the clear aperture. These aberrations limit scaling up the (millimeter size) clear aperture degrading significantly the overall MTF of the camera in which the LC lens is employed.

One of the factors limiting a clear aperture diameter of TLCLs is the degree to which the electrical field drop-off profile across the TLCL aperture mimics (or not) an electrical field profile required to produce a spherical wavefront profile illustrated in dashed line in FIG. 3.

General wisdom in the art is to employ geometries with a large number of electrical field control structures (also referred to as pixels) to compensate for deviations from the required profile. For example Yung-Yuan Kao, Paul C.-P. Chao, and Chieh-Wen Hsueh in "A New Low-Voltage-Driven GRIN Liquid Crystal Lens with Multiple Ring Electrodes in Unequal Widths", Optics Express, Vol. 18, No. 18, 30 Aug. 2010, exclusively concentrate on one control parameter and describe accounting for higher order deviations from a desired result by adding a large number of nested control structures or pixels. While some results have been achieved, such experimental attempts remain laboratory curiosities because such pixel structures suffer from low light transmission, and the corresponding complex manufacturing required suffers from very low yields particularly due to variable material properties at microscales, and further suffer from requiring complex auxiliary control components. Practice confirms that increasing the number of control structures minimizes manufacturing yield due to complex manufacturing and complex control requirements.

Returning to FIG. 2, in some implementations, different control signals can be applied to the flat electrodes 212a and 212b generating respective electric fields between flat electrodes 212a and 212b and the central control structure (hole patterned electrode) 326 using dual control signal generation circuits for independent wavefront adjustment control of each polarization. Without limiting the invention, the middle electrode structure 326 can have two hole patterned electrodes 214a and 214b, one on either side of a common substrate 211 and hole patterned electrodes 214a and 214b are associated with WCL 219a and 219b, respectively (as shown). From a manufacturing perspective, for LC full-lens polarization independent geometries, the mid substrate 211 can be implemented as two separate substrates, for example bonded by a thin layer of adhesive. The invention is not limited to such same thickness separate mid substrates.

In other implementations, the polarization-independent TLCL is driven by a single electrical driver. When a single control signal drive circuit is used for both LC cells, not only is the necessary number of layers reduced but also the number control signals and the complexity of auxiliary control components employed are reduced. For example the control signals can be applied between hole patterned electrodes 214a and 214b, and electrodes 212a and 212b. Without limiting the invention, either electrodes 214 or 212 can have a common electrical connection.

To have the desired properties relating to electric field shaping while allowing for the TLCL to be thin and operational at low voltage, WCL 219a and 219b includes a high electrical resistivity material having properties between those of a semiconductor and those of a dielectric. The material characteristics are in a range for which the fundamental mechanisms of material conductivity (and polarizability) suffer drastic transitions (sometimes called the percolation zone). In this percolation zone, layer conductivity changes drastically with small changes in WCL material volume, morphological structure/geometry, which severely limits repeatability in manufacturing weakly conductive layers. In the silicon semiconductor industry, control efficiency of sheet resistance is still in the order of ±10%, even less accurate for emerging technology using indium phosphide. Accordingly, conductive properties of the deposited layer of WCL material will vary greatly from wafer to wafer. Manufacturing the WCL 219a and 219b shown in FIG. 2 using conventional deposition technology is a challenge to produce a material composition, morphology and sheet thickness which provides the desired conductivity properties (including sheet resistance). For circuitry intended to control optical lens operation using a control signal having a predetermined range of frequencies, the range of acceptable sheet resistances of the WCL is limited.

The invention is not limited to the TLCL layered structures illustrated herein, while distinct WCL layers 219a and 219b are illustrated, when reference is made to a WCL hereinafter, such reference is defined to include sheet resistance dominated materials, variable conductivity, frequency dependent characteristic materials for example described in PCT application PCT/IB2009/052658 entitled "Electro-Optical Devices using Dynamic Reconfiguration of Effective Electrode Structures" filed Jun. 21, 2009, which is incorporated herein by reference, and in International Patent Application PCT/CA2011/050651 filed 14 Oct. 2011 entitled "In-Flight Auto Focus Method and System for Tunable Liquid Crystal Optical Element" claiming priority from U.S. Provisional Patent Application 61/424,946 filed Dec. 20, 2010, both of which are incorporated herein by reference, and doped liquid crystal layers for example described in PCT application PCT/IB2009/052658 entitled "Electro-Optical Devices using Dynamic Reconfiguration of Effective Electrode Structures" filed Jun. 21, 2009, which is also incorporated herein by reference.

In accordance with the proposed solution a more advanced wavefront adjustment profile, including spherical, is provided:

In some embodiments, a LC optical device includes: a first LC cell having a LC layer, a transparent planar electrode on a first side of the LC layer and a hole patterned electrode on a second side of the LC layer, opposite the planar electrode. The first LC cell also includes a weakly conductive layer adjacent to the hole patterned electrode. A second LC cell is provided which also has a LC layer, a planar electrode and a hole patterned electrode positioned, respectively, to the side of the LC layer (in reverse order with respect to that of the first LC cell). The second LC cell also has a weakly conductive layer adjacent to the hole patterned electrode of the second LC cell. In accordance with the proposed solution, a more advanced electric field profile approximation (including non-monotonic) is implemented using at least one control ring electrode and a floating electrode structure enabling an expansion of the clear aperture.

In other embodiments, the LC optical device is a TLCL having two LC lens cells, each with a weakly conductive layer. A common ring electrode is employed with the weakly conductive layers to shape the electric field to provide a Schmidt-like corrector plate wavefront adjustment.

In accordance with one aspect of the proposed solution, a LC optical device is provided comprising: a LC cell controlling optical properties of light passing therethrough, said LC cell having a LC layer; a planar electrode located to a first side of said LC layer; an electric field control structure located to a second side of said LC layer opposite said first side of said LC layer; and a wavefront adjustment structure configured to provide optical phase front adjustment. In some embodiments the wavefront adjustment structure is a conductive floating electrode.

In accordance with an aspect of the proposed solution, there is provided a LC gradient index optical device having a layered structure, the optical device including: at least two support substrates; an external hole patterned control electrode provided on one of said substrates and having an aperture; an internal hole patterned control electrode provided on one of said substrates within said aperture, said internal control electrode and said external control electrode being separated by a gap, said gap forming part of said aperture; a weakly conductive material provided on said one of said substrates over said aperture; a planar transparent electrode provided on another of said substrates; an alignment surface provided on said substrates over said electrodes; a layer of LC material contained by substrates and in contact with said alignment surface of said substrates; and a floating transparent electrode provided on a side of said one of said substrates opposite said external and said internal hole patterned electrode.

In accordance with a further aspect of the proposed solution, there is provided a LC gradient index optical device having a layered structure and having an aperture, the optical device including: at least two support substrates; a transparent internal hole patterned control electrode provided on one of said substrates within said aperture; a weakly conductive material provided on said one of said substrates over said aperture; a planar transparent electrode provided on another of said substrates; an alignment surface provided on said substrates over said electrodes; and a layer of LC material contained by substrates and in contact with said alignment surface of said substrates.

In accordance with yet another aspect of the proposed solution, there is provided a LC gradient index optical device having a layered structure and having an aperture, the optical device including: at least two support substrates; an external hole patterned control electrode provided on one of said substrates and having an aperture; a weakly conductive material layer provided on said one of said substrates wholly within said aperture; a planar transparent electrode provided on another of said substrates; an alignment surface provided on said substrates over said electrodes; and a layer of LC material contained by substrates and in contact with said alignment surface of said substrates.

In accordance with a further aspect of the proposed solution, there is provided a liquid crystal gradient index optical device having a layered structure, the optical device comprising: at least two support substrates; an external hole patterned control electrode provided on one of said substrates and having an aperture; an internal hole patterned control electrode provided on one of said substrates within said aperture, said internal control electrode and said external control electrode being separated by a gap, said gap forming part of said aperture; a weakly conductive material provided on said one of said substrates over said aperture; a planar transparent electrode provided on another of said substrates; an alignment surface provided on said substrates over said electrodes; a layer of liquid crystal material contained by substrates and in contact with said alignment surface of said substrates; and a floating transparent electrode provided on a side of said one of said substrates opposite said external and said internal hole patterned electrode.

In accordance with a further aspect of the proposed solution, there is provided an optical device, wherein said optical device is a circular lens, said external hole patterned electrode having a circular aperture and said internal hole patterned electrodes being annular.

In accordance with a further aspect of the proposed solution, there is provided an optical device, wherein said optical device is a cylindrical lens, said external and said internal hole patterned electrodes being parallel strips.

In accordance with a further aspect of the proposed solution, there is provided an optical device, further comprising a drive signal source connected to said external hole patterned electrode, to said internal hole patterned electrode and to said planar electrode, said drive signal source being configured to provide a first drive signal between said external hole patterned electrode and said planar electrode and a second drive signal between said internal hole patterned electrode and said planar electrode.

In accordance with a further aspect of the proposed solution, there is provided an optical device, wherein said first drive signal and said second drive signal have chosen characteristics to impart a substantially linear change in electric field between said external and said internal hole patterned electrodes.

In accordance with a further aspect of the proposed solution, there is provided an optical device, wherein said floating electrode is operative to help said drive signal source achieve an electric field having a parabolic profile in a central portion of said aperture.

In accordance with a further aspect of the proposed solution, there is provided an optical device, wherein said floating electrode is smaller than said external hole patterned electrode.

In accordance with a further aspect of the proposed solution, there is provided an optical device, wherein said floating electrode covers said aperture.

In accordance with a further aspect of the proposed solution, there is provided an optical device, wherein said geometry is doubled up to provide two single polarization optical devices stacked together with alignment layers arranged essentially orthogonally to provide focusing of two polarizations of light.

In accordance with a further aspect of the proposed solution, there is provided an optical device, wherein a single said floating electrode is provided between said two single polarization lenses.

In accordance with a further aspect of the proposed solution, there is provided an optical device, wherein said internal and external hole patterned electrodes are substantially coplanar, and said internal control electrode drive signal is applied to said internal hole patterned control electrode employing a plurality of lead conductors.

In accordance with a further aspect of the proposed solution, there is provided an optical device, wherein said external hole patterned electrode is contiguous and each lead conductor passes out of plane with respect to the external hole patterned electrode to provide said drive signal to the internal hole patterned electrode.

In accordance with a further aspect of the proposed solution, there is provided an optical device, wherein said external hole patterned electrode is segmented and each lead conductor passes in a plane of the external hole patterned electrode to provide said drive signal to the internal hole patterned electrode.

In accordance with a further aspect of the proposed solution, there is provided an optical device, wherein said signal source is further configured to provide independent drive signals to each external hole patterned electrode segment.

In accordance with a further aspect of the proposed solution, there is provided an optical device, wherein said signal source is further configured to drive said plurality of external hole patterned electrode segments for applying asymmetric phase profiles for light tilting, optical image stabilization, sub-pixel shifting, correcting a comma aberration and correcting astigmatism aberration.

In accordance with a further aspect of the proposed solution, there is provided an optical device, wherein said signal source is further configured to drive said internal hole patterned electrode and said plurality of external hole patterned electrode segments to provide temperature compensation.

In accordance with a further aspect of the proposed solution, there is provided an optical device, wherein said internal hole patterned electrode is transparent.

In accordance with a further aspect of the proposed solution, there is provided an optical device, wherein said external hole patterned electrode is one of an opaque and transparent.

In accordance with a further aspect of the proposed solution, there is provided an optical device, wherein said external hole patterned electrode participates in defining an aperture of said optical device In accordance with a further aspect of the proposed solution, there is provided an optical device, wherein said electric fields generated in said liquid crystal layers have substantially the same value.

In accordance with a further aspect of the proposed solution, there is provided a liquid crystal gradient index optical device having a layered structure and having an aperture, the optical device comprising: at least two support substrates; a transparent internal hole patterned control electrode provided on one of said substrates within said aperture; a weakly conductive material provided on said one of said substrates over said aperture; a planar transparent electrode provided on another of said substrates; an alignment surface provided on said substrates over said electrodes; and a layer of liquid crystal material contained by substrates and in contact with said alignment surface of said substrates.

In accordance with a further aspect of the proposed solution, there is provided an optical device, wherein said optical device is a Schmidt corrector plate for correcting a spherical lens, said internal hole patterned electrode comprising an annular ring electrode.

In accordance with a further aspect of the proposed solution, there is provided an optical device, wherein said optical device is a Schmidt-like corrector plate for correcting a cylindrical lens, said internal hole patterned electrode comprising a pair of parallel strips.

In accordance with a further aspect of the proposed solution, there is provided an optical device, further comprising a drive signal source connected to said internal hole patterned electrode and to said planar electrode, said drive signal source being configured to apply a drive signal between said internal hole patterned electrode and said planar electrode.

In accordance with a further aspect of the proposed solution, there is provided an optical device, wherein said drive signal is operative to help said drive signal source achieve an electric field having a sombrero profile across said aperture.

In accordance with a further aspect of the proposed solution, there is provided an optical device, wherein said geometry is doubled up to provide two single polarization optical devices stacked together with alignment layers arranged essentially orthogonally to provide correction of two polarizations of light.

In accordance with a further aspect of the proposed solution, there is provided an optical device, wherein said drive signal is applied to said internal hole patterned control electrode employing a at least one lead conductor.

In accordance with a further aspect of the proposed solution, there is provided an optical device, wherein said internal hole patterned electrode is contiguous.

In accordance with a further aspect of the proposed solution, there is provided an optical device, wherein said internal hole patterned electrode is segmented, each segment being driven via a lead conductor provide optical correction.

In accordance with a further aspect of the proposed solution, there is provided an optical device, wherein said signal source is further configured to provide independent drive signals to each external hole patterned electrode segment.

In accordance with a further aspect of the proposed solution, there is provided an optical device, wherein said signal source is further configured to drive said plurality of internal hole patterned electrode segments for applying asymmetric phase profiles for light tilting, optical image stabilization, sub-pixel shifting, correcting a comma aberration and correcting astigmatism aberration.

In accordance with a further aspect of the proposed solution, there is provided an optical device, wherein said signal source is further configured to drive said plurality of internal hole patterned electrode segments to provide temperature compensation.

In accordance with a further aspect of the proposed solution, there is provided a liquid crystal gradient index optical device having a layered structure and having an aperture, the optical device comprising: at least two support substrates; an external hole patterned control electrode provided on one of said substrates and having an aperture; a weakly conductive material layer provided on said one of said substrates wholly within said aperture; a planar transparent electrode provided on another of said substrates; an alignment surface provided on said substrates over said electrodes; and a layer of liquid crystal material contained by substrates and in contact with said alignment surface of said substrates.

In accordance with a further aspect of the proposed solution, there is provided an optical device, wherein said optical device is a circular lens, said external hole patterned electrode having a circular aperture and weakly conductive material layer being disk shaped.

In accordance with a further aspect of the proposed solution, there is provided an optical device as claimed in claim 33, wherein said optical device is a cylindrical lens, said external electrode being parallel strips and said weakly conductive material layer being elongated.

In accordance with a further aspect of the proposed solution, there is provided an optical device, further comprising a drive signal source connected to said external hole patterned electrode and to said planar electrode, said drive signal source being configured to provide a drive signal between said external hole patterned electrode and said planar electrode.

In accordance with a further aspect of the proposed solution, there is provided an optical device, wherein said weakly conductive material layer is operative to help said drive signal source achieve an electric field having a parabolic profile in a central portion of said aperture.

In accordance with a further aspect of the proposed solution, there is provided an optical device, wherein said geometry is doubled up to provide two single polarization optical devices stacked together with alignment layers arranged essentially orthogonally to provide focusing of two polarizations of light.

In accordance with a further aspect of the proposed solution, there is provided an optical device, wherein a single said weakly conductive layer is provided between said two single polarization lenses.

In accordance with a further aspect of the proposed solution, there is provided an optical device, wherein said external hole patterned electrode is segmented, wherein said signal source is further configured to provide independent drive signals to each external hole patterned electrode segment.

In accordance with a further aspect of the proposed solution, there is provided an optical device, wherein said signal source is further configured to drive said plurality of external hole patterned electrode segments for applying asymmetric phase profiles for light tilting, optical image stabilization, sub-pixel shifting, correcting a coma aberration and correcting astigmatism aberration.

In accordance with yet another aspect of the proposed solution, there is provided an optical device, wherein said signal source is further configured to drive said plurality of external hole patterned electrode segments to provide temperature compensation.

BRIEF DESCRIPTION OF THE DRAWINGS

The invention can be better understood by way of the following detailed description of embodiments of the invention with reference to the appended drawings, in which:

FIGS. 5 and 6 illustrate measured wavefront adjustment provided by a polarization independent tunable liquid crystal lens geometry illustrated in FIG. 4 in accordance with the proposed solution;

FIGS. 7A and 7B are schematic diagrams respectively illustrating polarization dependent top and cross-section views of the embodiment illustrated in FIG. 4, in accordance with the proposed solution;

FIG. 14 is a schematic diagram illustrating peripheral wavefront adjustment in accordance with the proposed solution;

DETAILED DESCRIPTION

Electric Field Control Structure Wavefront Adjustment

For millimeter size clear aperture TLCLs, experimental measurements have discovered driving voltage dependent Spherical Aberrations (SA) of orders 3, 5 and 7, and RMS aberrations having submicron amplitudes.

The proposed solution includes tunable LC optical device control aspects which synergistically enhance wavefront adjustment. When the tunable LC optical device is a TLCL, the control aspects combine to enhance sphericity of wavefront adjustment for focusing an incident polarization-independent wavefront.

Aspects of the proposed solution are described first and presented along with experimental results. Enabling effects of the control aspects employed are described last in top-down fashion.

Advanced Wavefront Adjustment

Figure 4:
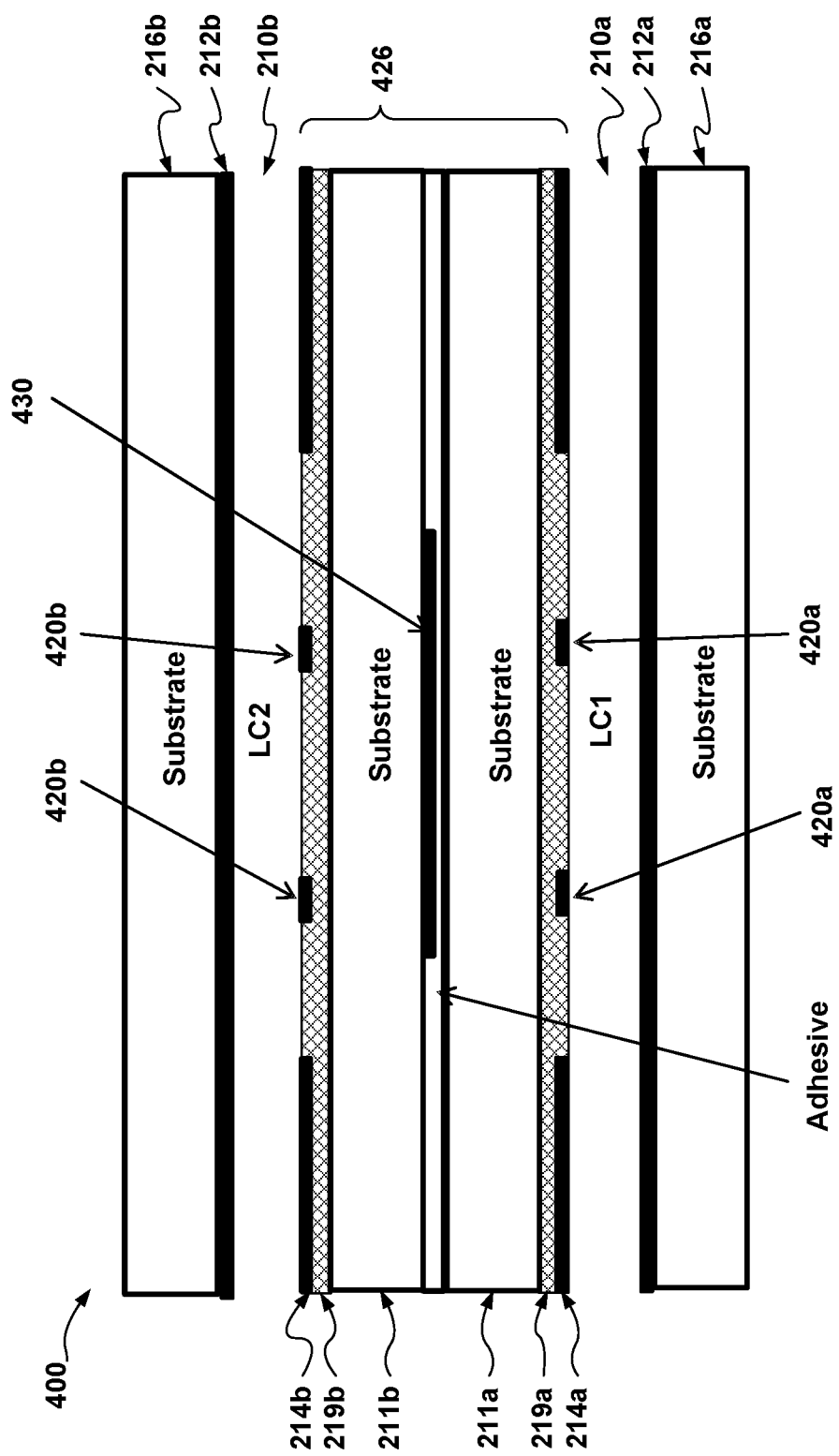
FIG. 4 is a schematic diagram illustrating a layered structure of polarization-independent optical device in accordance with an embodiment of the proposed solution.

FIG. 4 is a schematic diagram (not to scale) illustrating a layered structure 400 of an optical device in accordance with an embodiment of the proposed solution employing both a floating conductive central electrode 430 and internal donut shaped control electrodes 420a and 420b in a polarization independent optical device geometry.

FIG. 5 illustrates measured wavefront adjustment provided by a full TLCL implemented in accordance with the geometry illustrated in FIG. 4 having an external control electrode diameter (ARD) of 3.1 mm, compared against measured wavefront adjustment provided by a full TLCL implemented in accordance with the same geometry however without the internal annular ring control electrodes 420a and 420b (more on this later), and against a spherical wavefront profile in dashed line (the aspect ratio has been sacrificed in order to exaggerate spherical departures/errors), all at 2 Diopter optical power. With a 2 mm conductive floating disk electrode 430 alone, and using external hole patterned electrode drive signal $V_1$ (5V, 8.5 kHz), the wavefront adjustment profile provided is substantially spherical in the center and a 0.12 μm RMS aberration on the periphery. The combination of a large conductive floating disk electrode 430 substantially covering the opening of the hole patterned electrode 214(a, b) and annular ring shaped control electrode 420(a, b) of a 2.6 mm diameter and 100 μm wide, driven with hole patterned control ring electrode drive signal $V_1$ (5V, 6 kHz) and the internal annular ring control electrode drive signal $V_2$ (1.3V, 6 kHz), provides a reduction in the measured RMS aberration in the order of 0.0027 μm. While it is preferred to use a drive circuit that delivers independent drive signals to the inner ring electrode and the outer hole patterned electrode, it is possible to use a coupler to deliver from a single signal source the two control signals. It is noted FIG. 4 is not to scale, as the geometry parameters specified herein immediately above place the internal annular ring control electrode 420(a, b) substantially closer to the inner edge of the hole patterned electrode 214(a, b).

FIG. 6 illustrates measured wavefront adjustment provided by a full TLCL implemented in accordance with the same geometry illustrated in FIG. 4 compared against measured wavefront adjustment provided by a full TLCL implemented in accordance with the same geometry as in FIG. 5 all at 4 Diopter optical power. With the floating conductive disk electrode 430 alone, where the hole patterned control electrode 214(a, b) is driven with drive signal $V_1$ (5V, 16.5 kHz), the wavefront adjustment profile provided is substantially spherical in the center and a 0.3 μm RMS aberration on the periphery. The combination of the floating conductive disk electrode 430 and annular ring shaped control electrode 420(a, b) provides a reduction in the measured RMS aberration in the order of 0.08 μm employing an external hole patterned control ring electrode drive signal $V_1$ (5V, 11.5 kHz) and an internal annular ring control electrode drive signal $V_2$ (2.52V, 11.5 kHz).

Figure 7C:
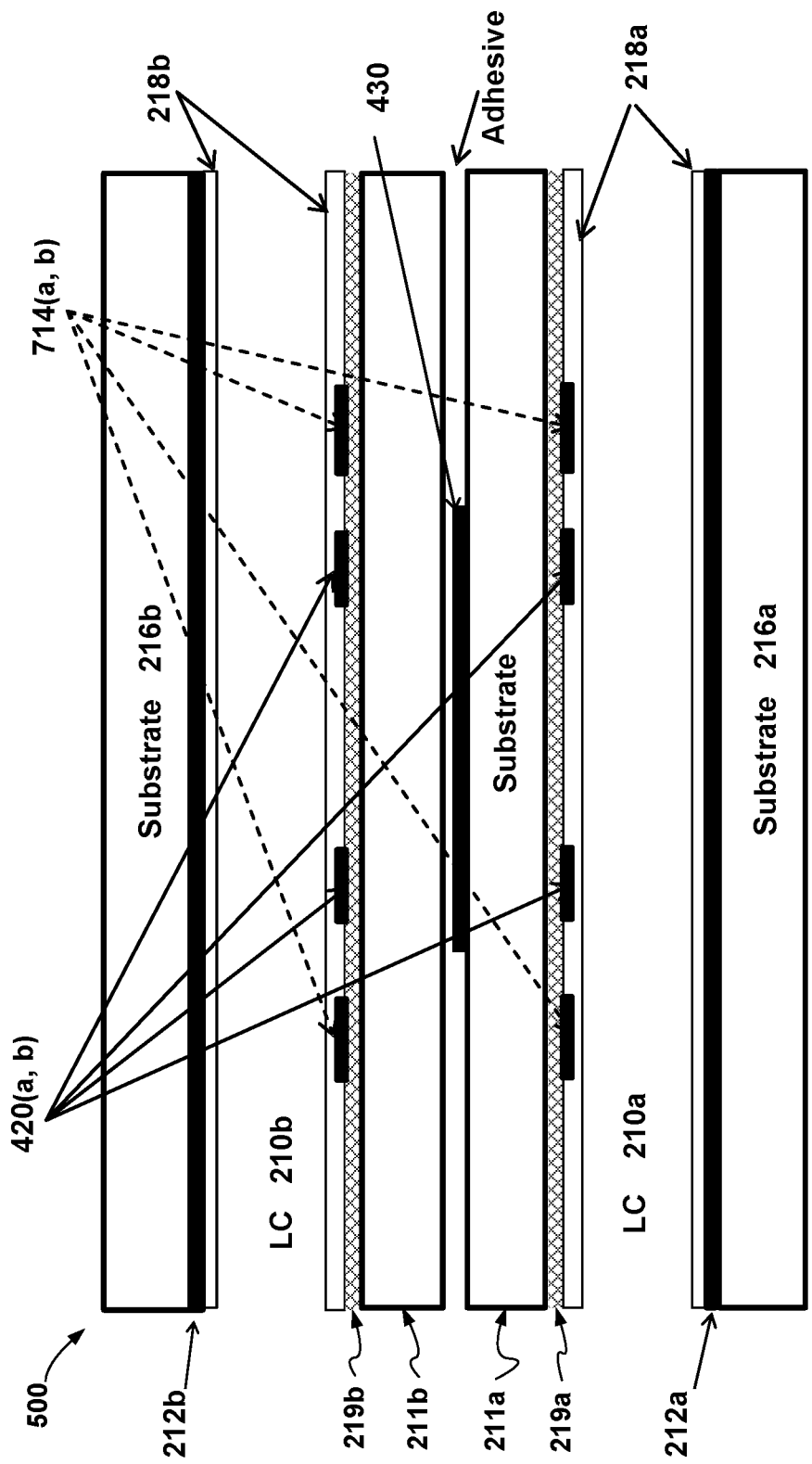
FIG. 7C is a schematic diagram illustrating a polarization independent geometry of the embodiment illustrated in FIGS. 7A and 7B in accordance with the proposed solution.
Figure 8:
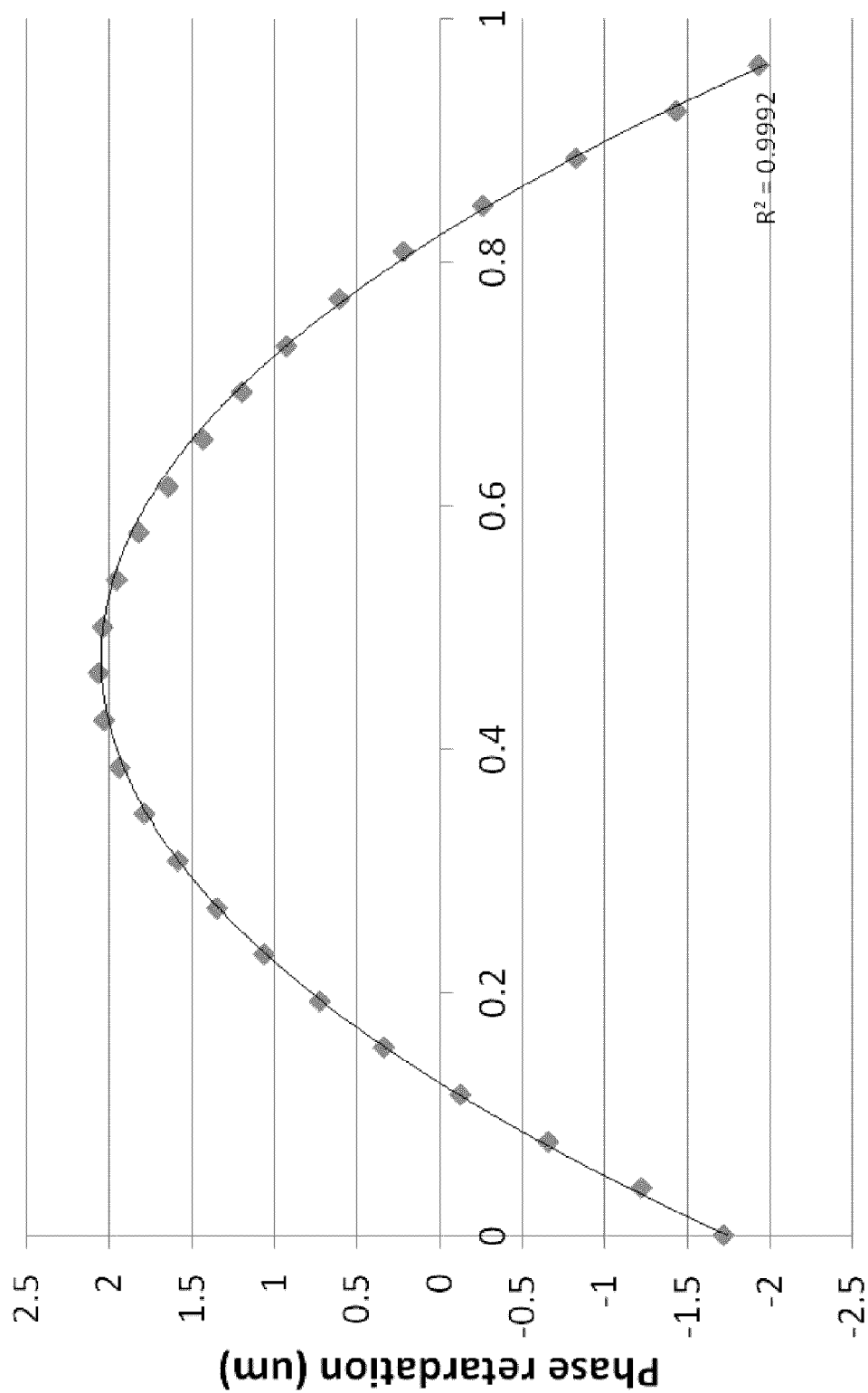
FIG. 8 is a graph illustrating, in accordance with the proposed solution, a wave retardation profile measured for the variant illustrated in FIG. 5.

In accordance with another implementation of this embodiment of the proposed solution, finer wavefront adjustment control is provided by employing an annular ring shaped external control electrode 714 in a geometry 500 as illustrated in FIGS. 7A and 7B for a half TLCL optical device and in FIG. 7B for a full TLCL optical device. For certainty, the invention is not limited to TLCLs and can be applied to other optical devices with an appropriate change in device geometry, for example the proposed solution can be applied to a cylindrical lens employing internal and external pairs of elongated strip electrodes. Advantageously, the additional control parameters including the width of the external annular ring shaped control electrode 714(a, b) and the relative position thereof with respect to the inner annular ring shaped control electrode 420(a, b) provide further configuration of the wavefront adjustment profile without additional auxiliary control structures such as but not limited to drive signal generation and supply components. An improved measured wave retardation profile is illustrated in FIG. 8 plotted against a spherical fit. Conformance can be determined by fitting the measured data points to the graph of the desired profile where an $R^2=1$ corresponds to measurements having a perfect fit across the aperture.

Surprisingly, FIG. 8 illustrates an $R^2$ of 0.9992 for a half TLCL geometry as illustrated in FIGS. 7A and 7B at 4 Diopter optical power which correspond to RMS aberrations in the order of 0.067 μm. These low aberrations are about 3.5 times less than previously achieved aberrations in half TLCL geometries which do not employ an inner annular ring shaped control electrode 420. Such experimental data provides support for an increase in the clear aperture.

Figures 9A, 9B:
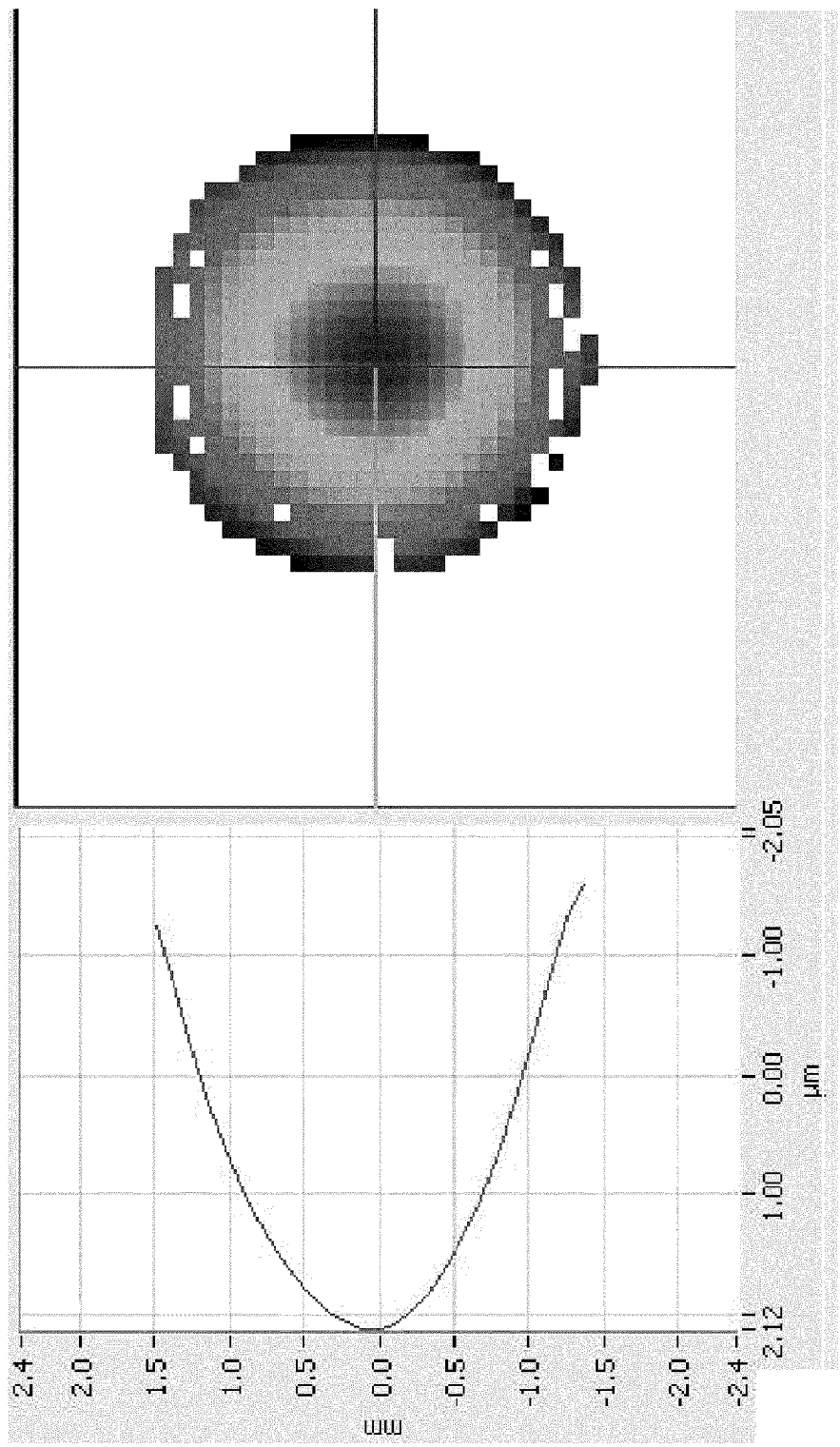
FIG. 9A illustrates, in accordance with yet another embodiment of the proposed solution, a snapshot from an Shack-Hartman (S-H) sensor screen for a half TLCL as illustrated in FIG. 7A.
FIG. 9B is a graph illustrating, in accordance with the proposed solution, a wave retardation profile measured for the embodiment illustrated in FIG. 9A.

In accordance with another embodiment of the proposed solution, FIG. 9A illustrates a snapshot from an Shack-Hartman sensor screen for a half TLCL as illustrated in FIGS. 7A and 7B at 4 Diopter optical power where the donut shaped control electrode 714 is transparent and segmented to permit passage of multiple lead conductors to make electrical connection with the internal annular ring shaped control electrode 420 substantially in the same plane in the layered structure. A gap is formed between the internal annular ring control electrode 420 and the external annular ring electrode 714. Other structures (not shown) in the layered geometry define the aperture of the TLCL optical device. In some implementations the gap between the inner 420 and external 714 control electrodes is within the aperture of the optical device. FIG. 9B graphically illustrates the corresponding wave retardation profile having an (improved) increased clear aperture compared to the profile illustrated in FIG. 8.

Figure 10:
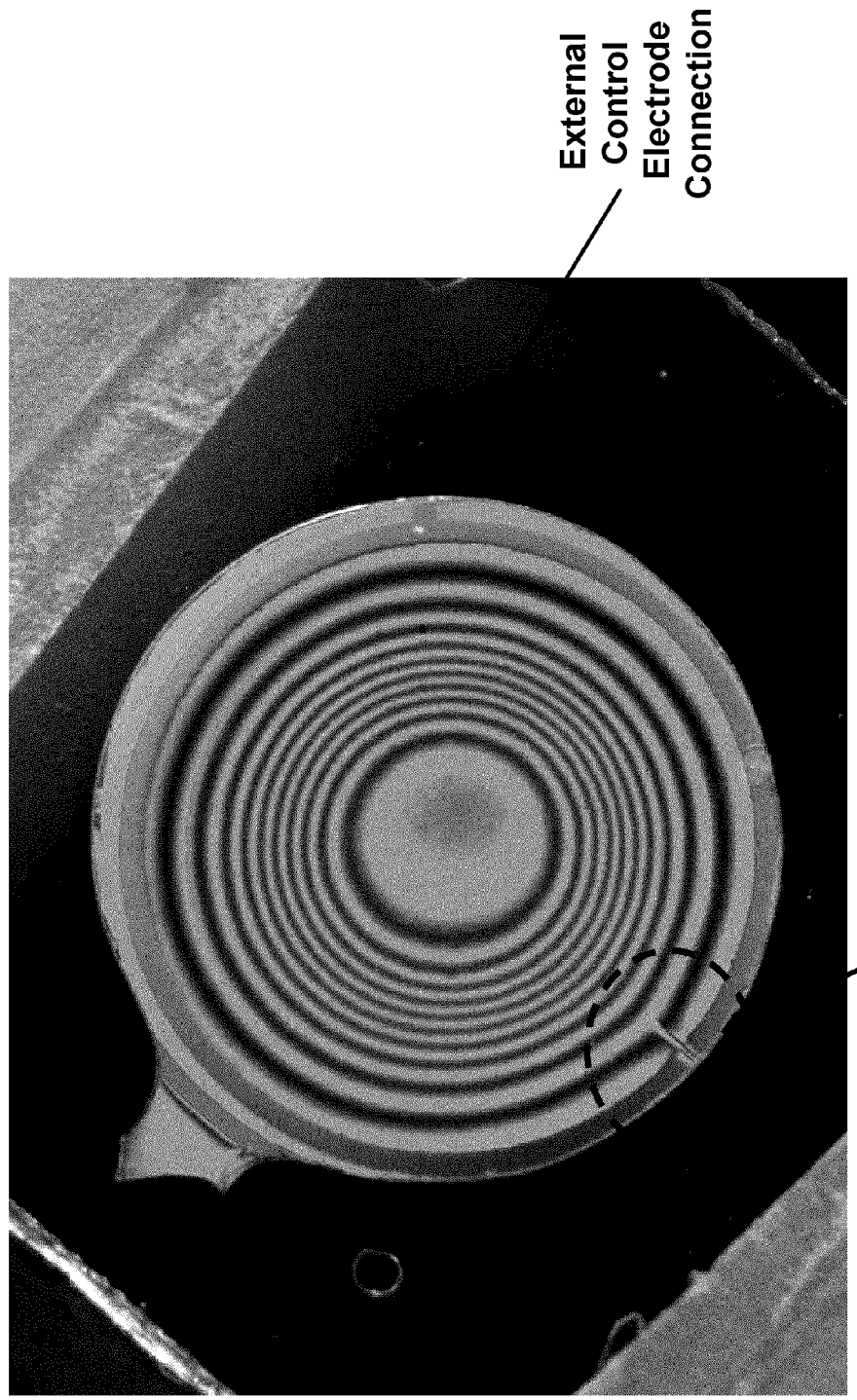
FIG. 10 is a diagram illustrating a fringe pattern corresponding to the Shack-Hartman (SH) wave front sensor snapshot illustrated in FIG. 9A, in accordance with the proposed solution.

FIG. 10 illustrates the fringe pattern corresponding to the Shack-Hartman (SH) wave front sensor snapshot illustrated in FIG. 9A with fringe distortions pointed out for a TLCL geometry such as illustrated in FIG. 7A. Fringe pinching is pointed out for a lead conductor passing through the gap in the external annular ring control electrode 714, and a departure from fringe circularity is pointed out for an electrical connection used to drive the annular ring shaped control electrode. The fringe pattern substantially corresponds to one providing a substantially spherical wavefront adjustment with negligible distortions for a half TLCL employing a driving signal having 7 kHz frequency and 5V RMS amplitude. In a full TLCL, such low voltage operation can be provided by the proximity of the electric field control structures including the internal 420, external 714 control electrodes and WCL to the LC layer while the common floating conductive disk electrode 430 synergistically participates in rounding the wavefront adjustment overall.

Figure 11:
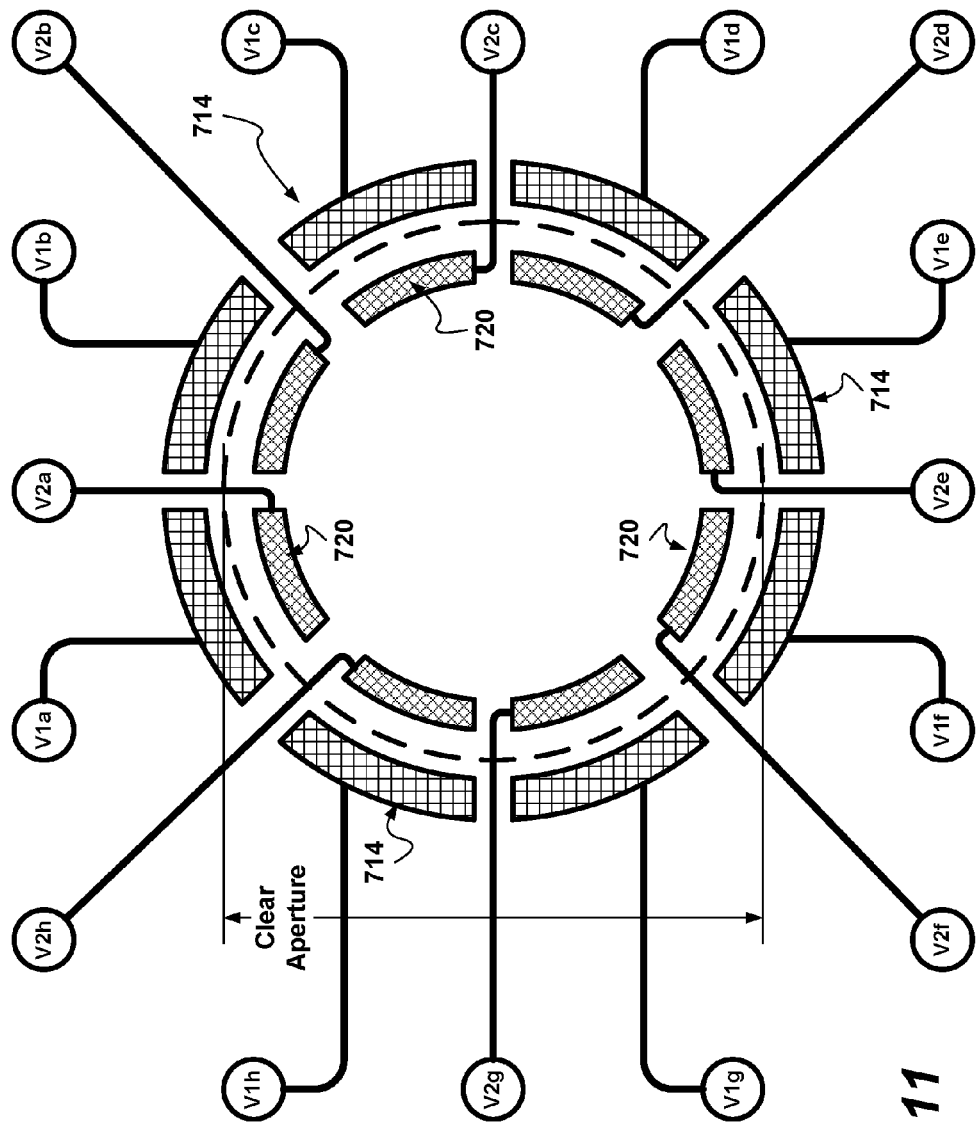
FIG. 11 is a diagram illustrating a top plan view of the liquid crystal lens of FIG. 7A, in accordance with another implementation of the proposed solution.

Both FIGS. 8 and 9B show small aberrations such as small wavefront tilt, some astigmatism and/or some coma stemming from manufacturing imperfections. FIG. 11 illustrates a top plan view of a LC lens having a layer geometry as illustrated in FIGS. 7A to 7C, in accordance with another implementation of the proposed solution. The hole patterned electrode 714 has a segmented geometry as described in the related PCT/CA2010/002023 International PCT Application, which is incorporated herein by reference, and can be employed, with the auxiliary control elements described therein, to remove undesirable focus tilt, astigmatism, comma, etc. manufacturing errors. The multiple lead conductors, a through h, applying $V_2$ to the inner donut ring control electrode 720 can be wafer manufactured (deposited) in the same plane with the inner donut ring control electrode 720 and the segments of the hole patterned ring control electrode 714.

In some implementations, of the above described layered geometries, the drive signal amplitudes applied to the annular ring electrodes 420/720, 714 and top and bottom flat electrodes 212(a, b) have a substantially linear relationship. It has been discovered that employing similar drive signal regimes reduces dependency on the floating disk conductive electrode 430 diameter and therefore desirably reduces manufacturing tolerances therefor. For some waveform profile requirements, the floating conductive electrode 430 can be larger than the optical device aperture.

Improved results can be achieved for large scale wafer production of TLCLs by calibrating control drive signal(s) applied to the hole patterned electrode 714 which are kept substantially constant during operation (save perhaps for compensating temperature induced distortions and the like) while the amplitude and frequency of the inner annular ring electrode 420/720(a, b) are varied for the optical device to exhibit an optical power.

Peripheral Wavefront Adjustment Profile Improvement

Figure 2:
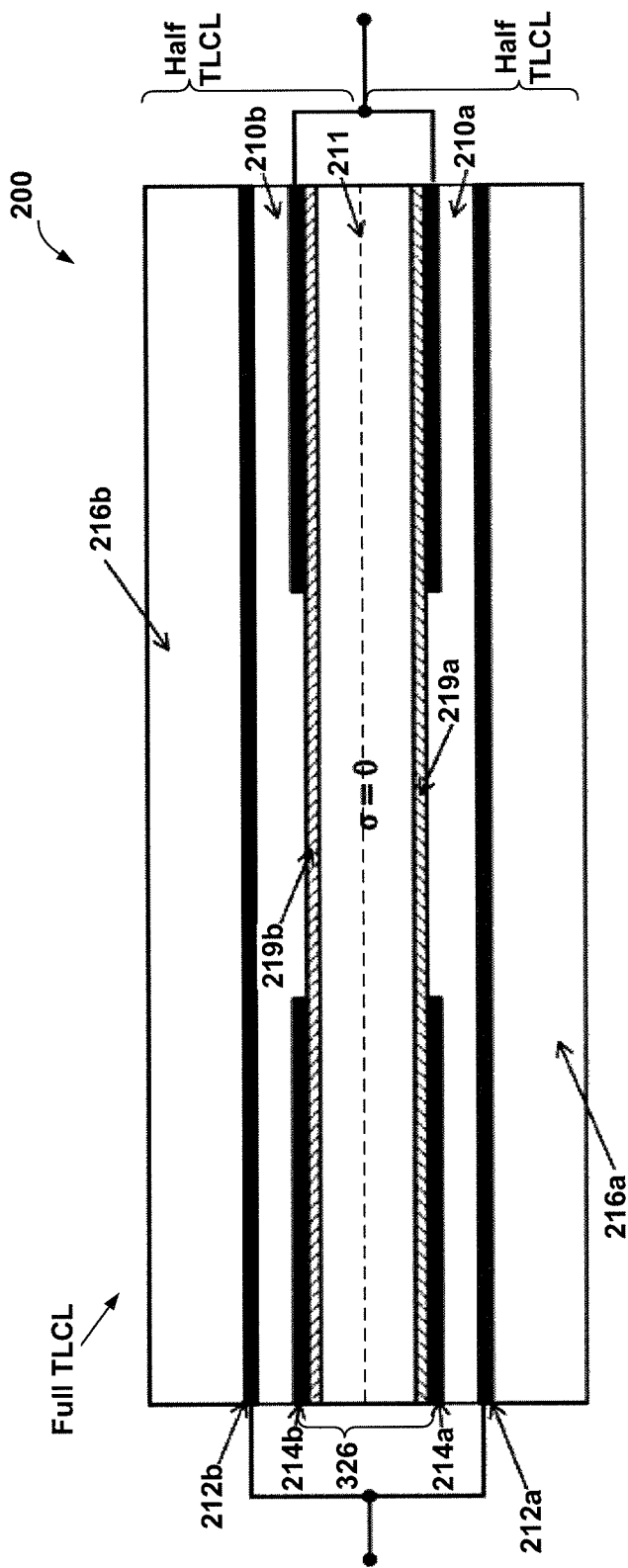
FIG. 2 is a schematic representation of a polarization independent LC lens, having a common electric field control structure, in accordance with the proposed solution.

It has been discovered that a conductive tape electrode alone, to which a separate driving signal is applied, can be used to reshape the wavefront adjustment profile otherwise generated by the electric field control structure combination of a hole patterned electrode 214(a, b) and weakly conductive layer 219(a, b) of FIG. 2. Depending on a TLCL layered structure geometry and material properties, such an annular ring-shaped conductive electrode can be employed to reshape the wavefront adjustment profile generated by the electric field control structure combination of a hole patterned electrode and weakly conductive layer of FIG. 2 towards a desired spherical wavefront adjustment profile, to improve sphericity of the wavefront, for example schematically illustrated by the dashed line in FIG. 3, particularly on the periphery.

Figure 12:
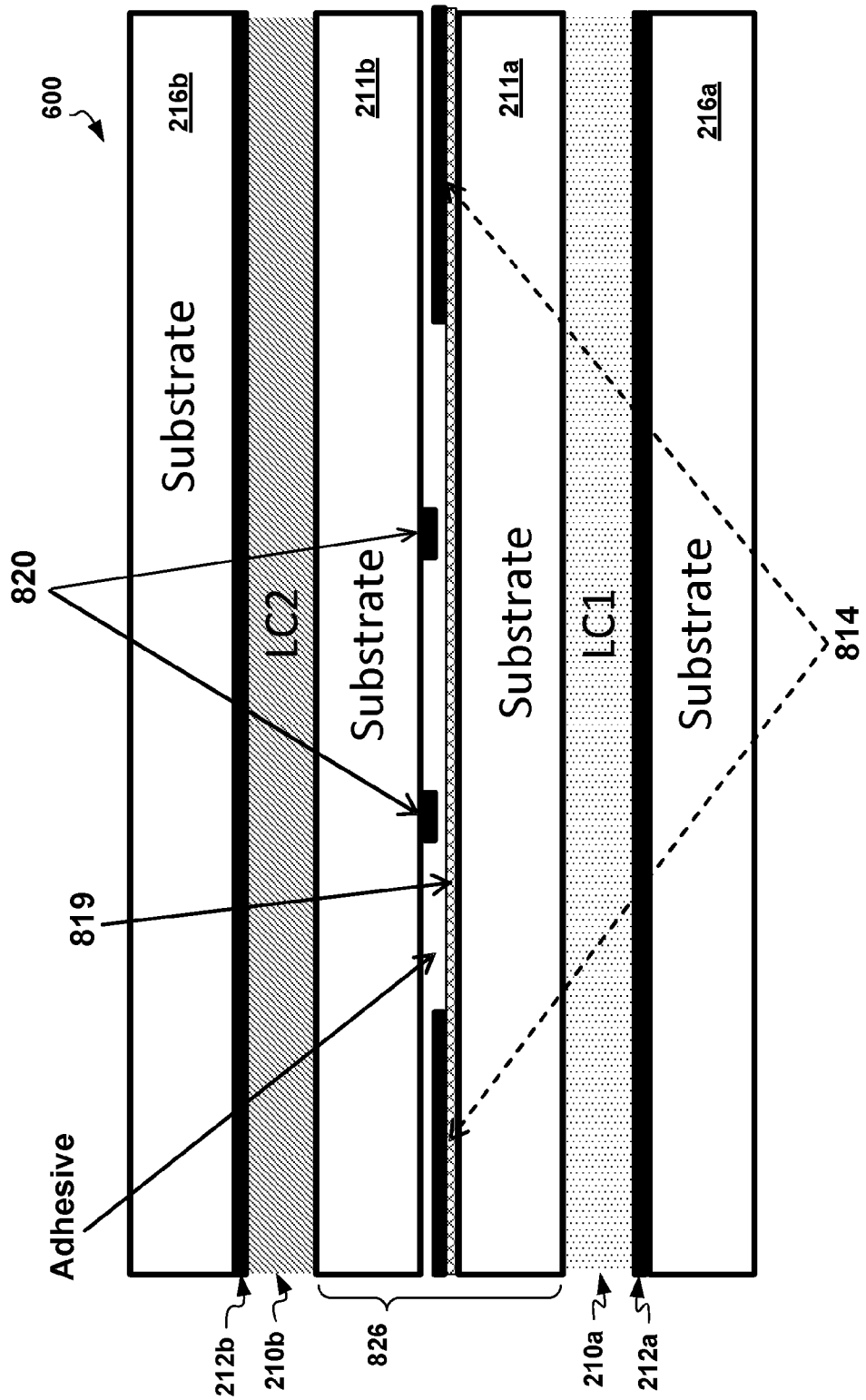
FIG. 12 is a schematic diagram illustrating a polarization independent layered optical device structure employing a single donut or ring shaped control electrode interior to a hole patterned electrode and a single weakly conductive layer to synchronously operate two LC cells, in accordance with one implementation of the proposed solution.

FIG. 12 illustrates a polarization independent full TLCL layered structure 600 having a central electrical field control structure 826, employing a single central hole patterned ring electrode and a single weakly conductive layer to synchronously operate both LC half-lenses as described in PCT application PCT/IB2009/052658 entitled "Electro-Optical Devices using Dynamic Reconfiguration of Effective Electrode Structures" filed Jun. 21, 2009, and in International Patent Application PCT/CA2011/050651 filed 14 Oct. 2011 entitled "In-Flight Auto Focus Method and System for Tunable Liquid Crystal Optical Element" claiming priority from US Provisional Patent Application 61/424,946 filed Dec. 20, 2010, all of which are incorporated herein by reference. A single WCL layer 819 preferably, but not necessarily, including a frequency dependent material is employed with a single hole patterned ring electrode 814 common to both LC half-lenses to synchronously control electric fields on either side of the central ring-shaped hole patterned electrode 814 between the central hole patterned electrode 814 and flat electrodes 212a and 212b on the outer sides of each LC half-lens.

In accordance with an embodiment of the proposed solution, FIG. 12 generically illustrates a donut shaped layer 820 in electrical contact with the common WCL layer 819 of the polarization independent optical device structure. Preferably the donut shaped layer 820 is non-dielectric in composition, including conductor or semiconductor materials, and as such can be an electrically driven controlled electrode employed to change the wavefront phase profile towards a desired spherical phase profile. Donut shaped electrodes (820) tend to affect (in cross-section) the peripheral part of the electric field:

In the case of a TLCL optical device, the internal control electrode 820 is annular ring shaped, and can be located along the optical path within the hole patterned ring electrode (814) diameter, and possibly within the clear aperture of the TLCL (see FIGS. 7A and 7B). Without limiting the invention, the internal annular ring shaped control electrode 820 is preferably transparent. However in some implementations the annular ring control electrode 820 can participate in defining the optical aperture of the overall optical device, in which case the conductive annular ring control electrode 820 may not be wholly transparent.

The invention is not limited to TLCLs, for example in the case of a cylindrical lens optical device, FIG. 12 is representative of a transverse cross-section perpendicular to the longitudinal direction of such cylindrical lens, and the internal control electrode 820 includes two parallel flat conductive strips parallel to the external hole patterned electrode 814 forming an elongated slit (into the page).

From a manufacturing perspective, FIG. 12 illustrates a polarization-independent optical device geometry produced by employing two polarization dependent optical devices having a geometry wherein the donut shaped control electrode 820 is manufactured on substrate 211b. While the donut shaped control electrode 820 is illustrated in proximity of, and separated by adhesive from the WCL 819, in FIG. 12 the invention is not limited thereto. The donut shaped control electrode 820 can also be implemented (not shown) in a geometry wherein the donut shaped control electrode 820 is deposited on an intermediary substrate during manufacturing.

Figure 13:
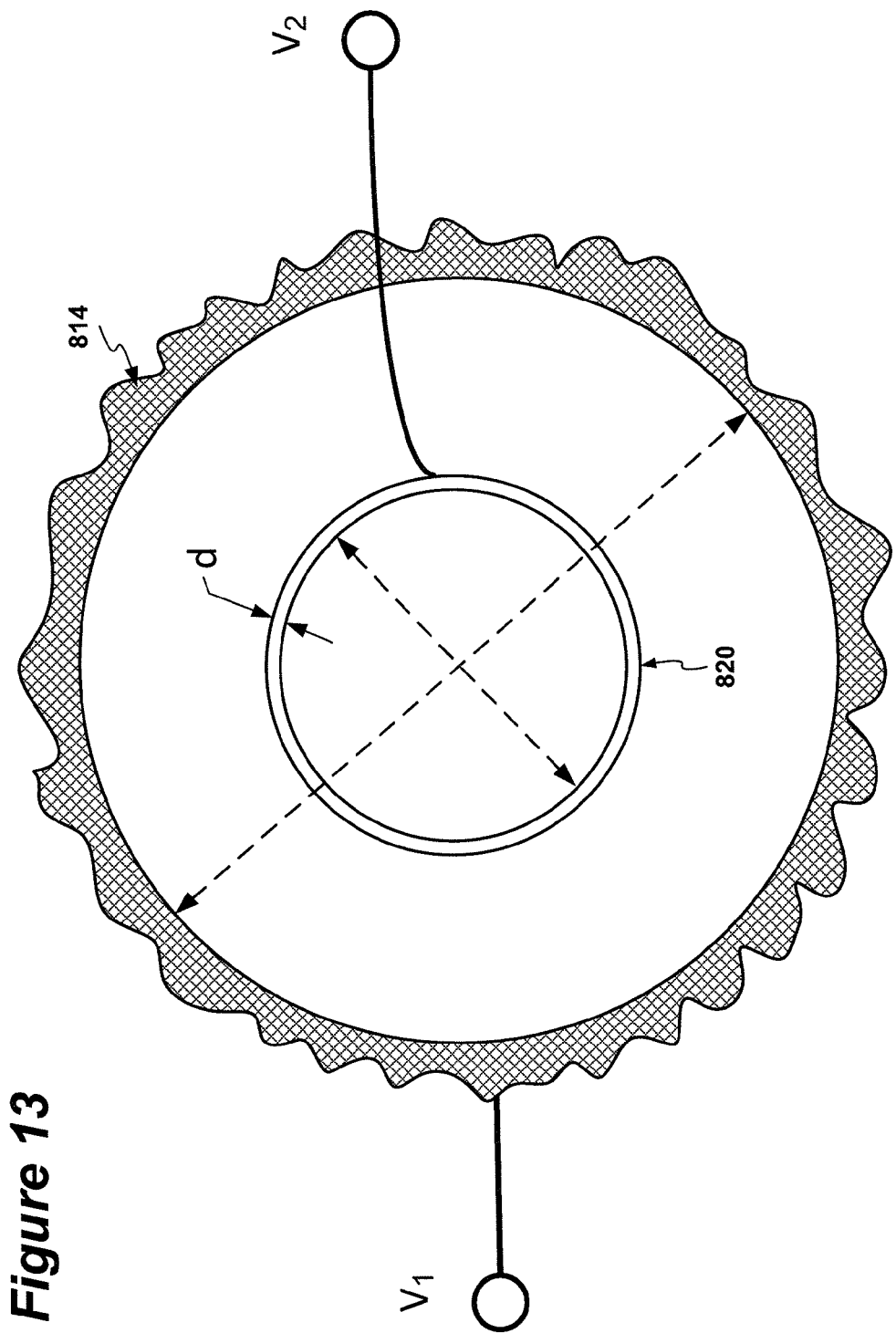
FIG. 13 is a schematic top view of the electric field control structure of the optical device illustrated in FIG. 12, in accordance with the proposed solution.

FIG. 13 illustrates plan view detail of the electric field control structure of a TLCL optical device as illustrated in FIG. 12. The hole patterned electrode 814 is shaped to produce a lensing effect and can define the clear aperture of the TLCL. It is noted that FIG. 13 does not show components to scale but is illustrative of component relationships within the overall geometry. The hole patterned electrode 814 can be opaque or transparent and is external to the internal annular ring shaped control electrode 820. In some implementations, the internal annular ring control electrode 820 can be located wholly within the clear aperture of the TLCL having a ring (tape) width d and therefore can be substantially transparent for example made of ITO. In other implementations, the internal annular ring control electrode 820 can be located adjacent to the periphery of the clear aperture of the TLCL in which case the internal annular ring control electrode 820 need not be wholly transparent. The internal annular ring electrode 820 can participate in defining the clear aperture of the TLCL. FIG. 13 also illustrates independent drive of the hole patterned electrode 814 and of the internal annular ring control electrode 820 to which independent control signals $V_1$ and $V_2$ are applied. Control signals $V_1$ and $V_2$ can include different amplitudes and/or different frequencies. A phase difference between control signals $V_1$ and $V_2$ can also be used to control the electrical field(s) generated.

FIG. 14 illustrates (in cross-section) peripheral wavefront adjustment provided, in accordance with the proposed solution, by an internal donut shaped electrode 820 employed with an hole patterned electrode 814 in an optical device geometry as illustrated in FIGS. 12 and 13. Driving signals $V_1$, $V_2$ and the location of the internal ring shaped electrode 820 can be configured to reduce the flare of the electric field on the periphery of the aperture of the optical device. In a TLCL optical device, the electric field adjustment is radial and the otherwise peripheral flare can be corrected to improve the sphericity of the wavefront adjustment provided. Similarly, in a cylindrical lens optical device, the electric field adjustment is lateral and the otherwise longitudinal edge flare can be corrected to improve the cylindricity of the wavefront adjustment provided.

Figure 15A:
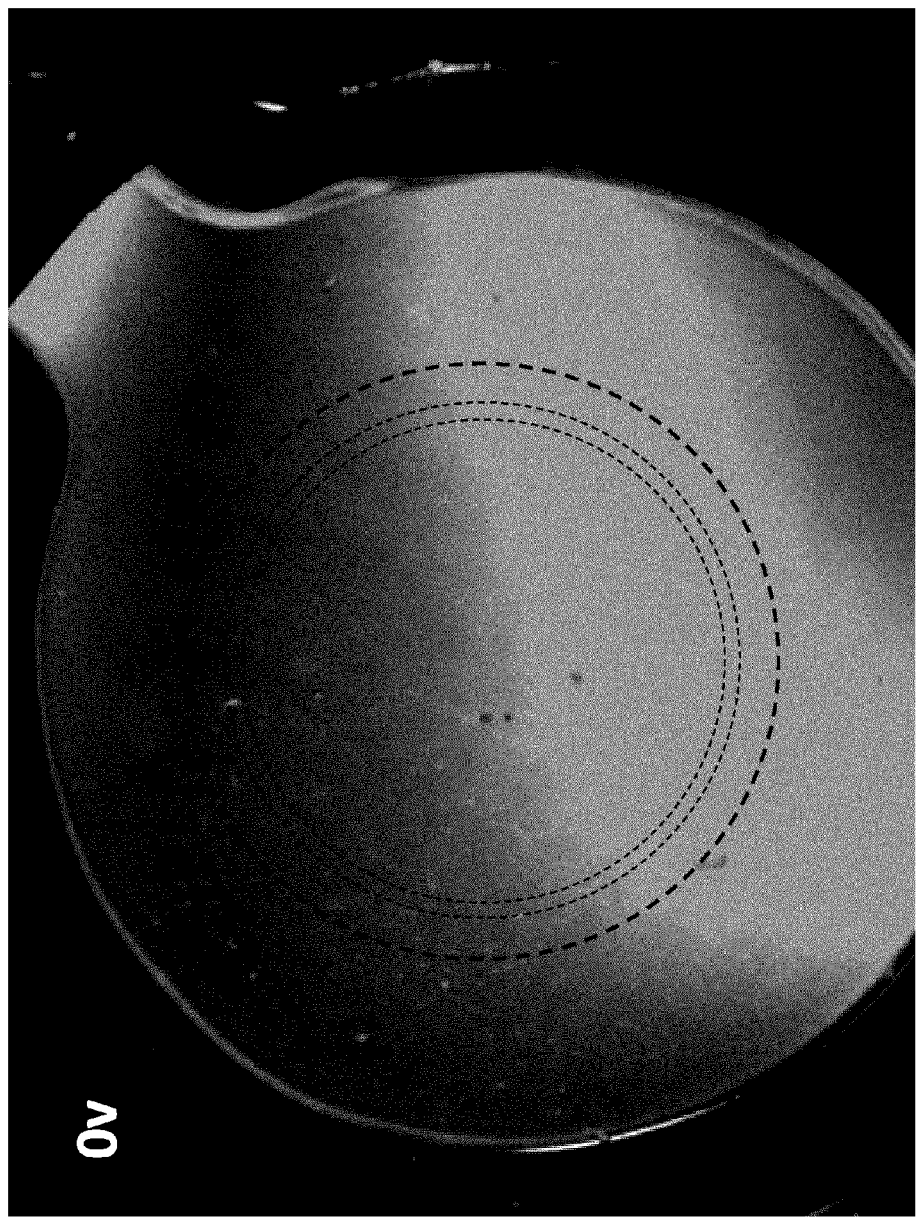
FIGS. 15A, 15B and 15C illustrate experimental peripheral wavefront adjustment results provided by an electric field control structure as illustrated in FIGS. 12 to 14 in accordance with the proposed solution.
Figure 15B:
Figure 15C:
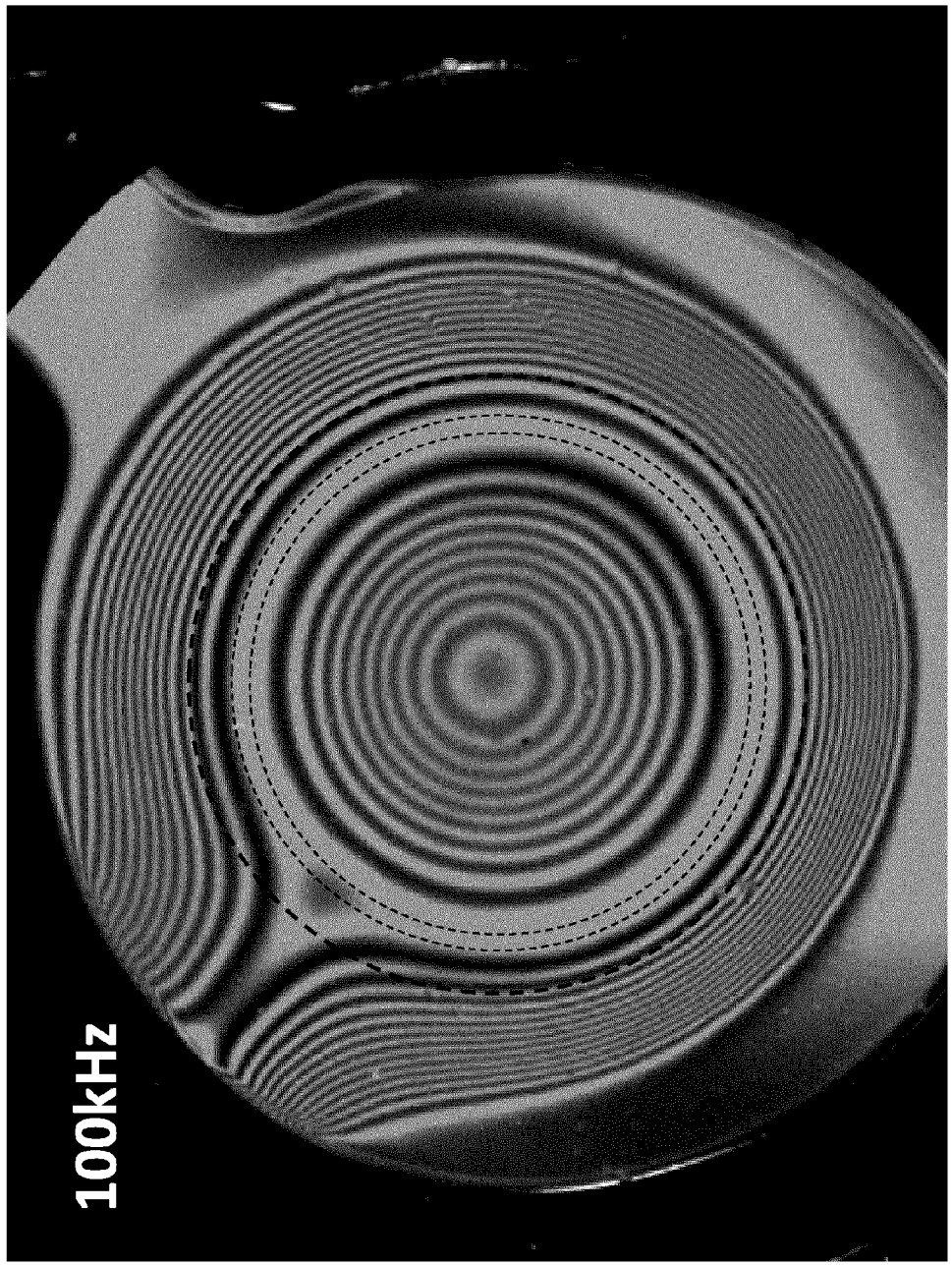

FIGS. 15A, 15B and 15C illustrate experimental peripheral wavefront adjustment results provided by an electric field control structure as illustrated in FIGS. 12 to 14 in accordance with the proposed solution.

FIG. 15A illustrates a substantially flat wavefront adjustment, within manufacturing tolerances. The outer dashed line represents the inner extent of the hole patterned ring control electrode 814 of FIG. 13 driven with a 0V amplitude drive signal $V_1$ and the pair of inner dashed lines represent the extent of the internal annular ring shaped control electrode 820 of FIG. 13 also driven with a 0V amplitude drive signal $V_2$. Both internal annular ring shaped electrode 820 and the hole patterned ring control electrode 814 are transparent ITO.

FIG. 15B illustrates the effect of applying low frequency 1 kHz drive signals $V_1$, $V_2$ to the control electrodes of the TLCL. The wavefront adjustment remains substantially flat in the middle while each peripheral fringe indicates one wavelength (difference) retardation wavefront adjustment. It is noted that a circular central region is substantially aberration free, with aberrations on the periphery most of which are beyond the internal annular ring control electrode 820.

Depending on the tolerable optical distortion, the clear aperture can extend substantially to the outer boundary of the internal annular ring control electrode 820. A more pronounced distortion is apparent in the top left corner as a pinching of fringes, which distortion is produced by a lead conductor crossing over the hole pattered electrode 814 providing drive signal $V_2$ to the internal annular ring control electrode 820.

FIG. 15C illustrates the effect of applying drive signals $V_1$, $V_2$ in the 100 kHz range to the control electrodes of the TLCL. The wavefront adjustment provides increasing wavelength retardation towards the middle where each fringe indicates one wavelength difference to converge incident light. The circularity of the fringes within the aperture attest to limited distortions created by the lead conductor providing the drive signal $V_2$ relegated to the periphery.

Figure 16:
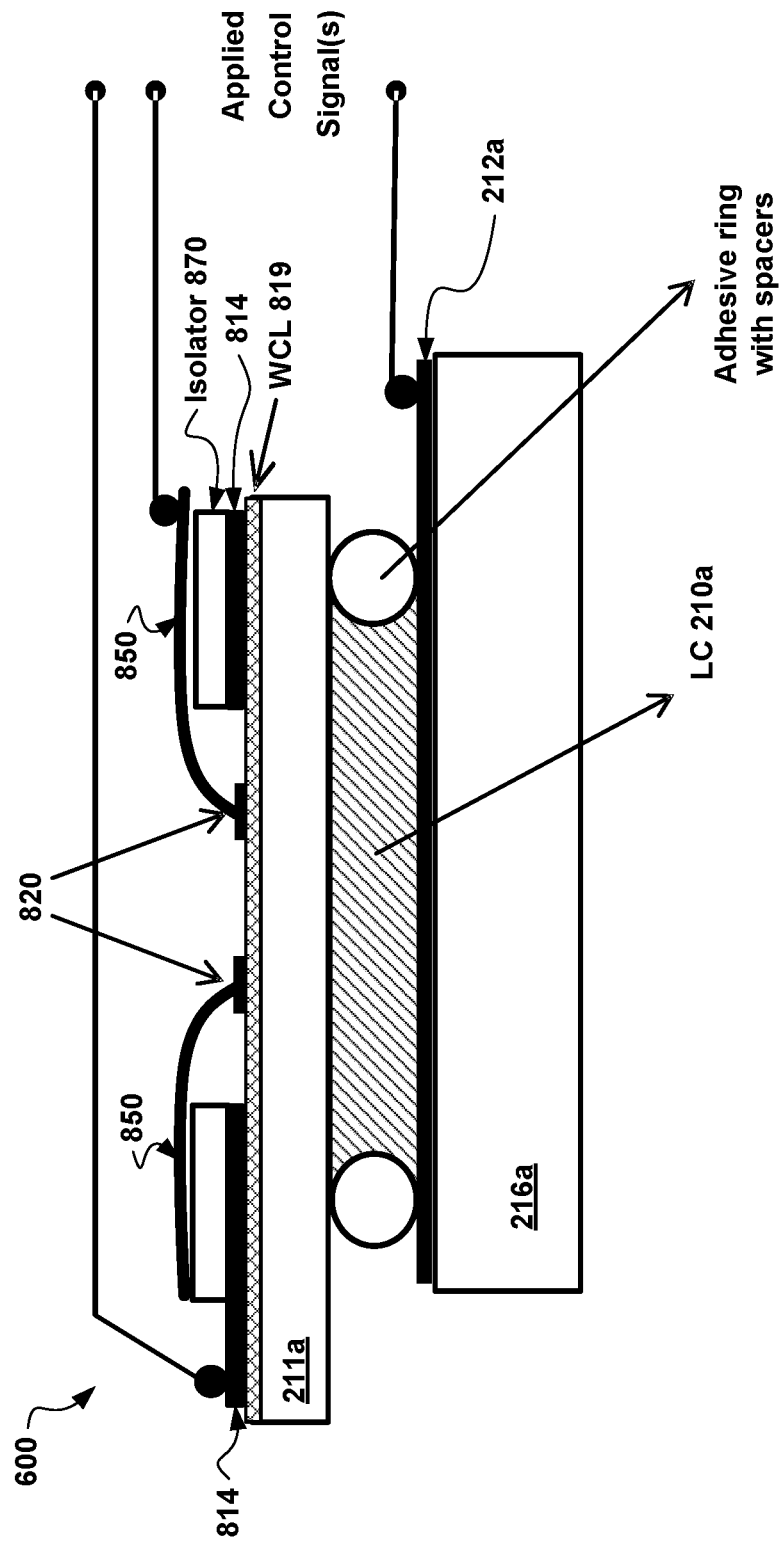
FIG. 16 is a schematic cross-sectional view of the electric field control structure of an optical device in accordance with another implementation the proposed solution.

In accordance with another implementation of the embodiment of the proposed solution, alternate connectivity geometries 600 can be employed to provide a more symmetric wavefront adjustment by using multiple lead conductors providing drive signal $V_2$ for example via four lead conductors 850 as illustrated in FIG. 16.

Figure 17A:
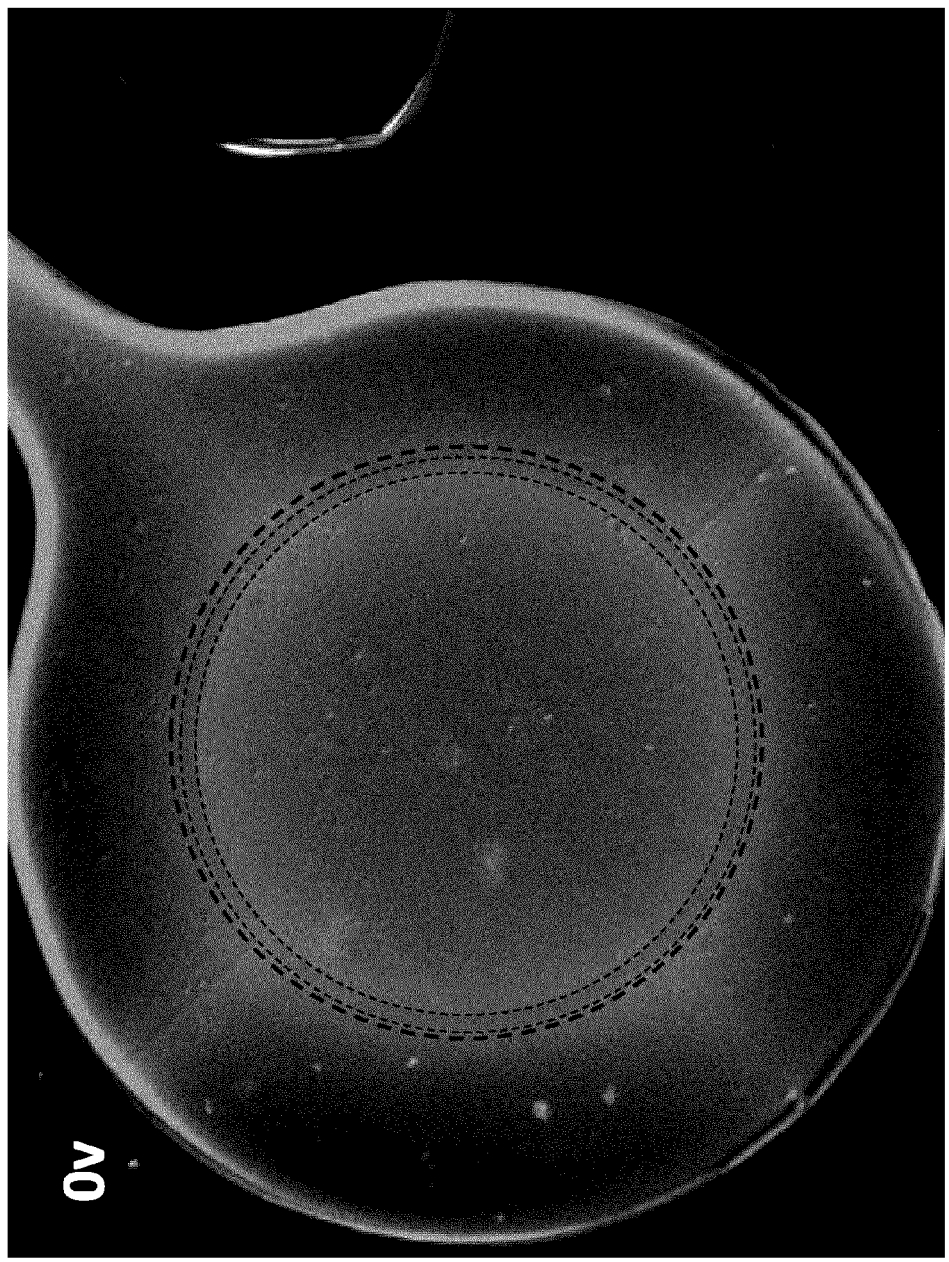
FIGS. 17A and 17B illustrate experimental peripheral wavefront adjustment results provided by an electric field control structure as illustrated in FIG. 16, in accordance with the proposed solution.

For example, by using four lead conductors 850 (only two illustrated in cross-section view) instead of one to deliver driving signal $V_2$ to the same internal annular ring control electrode 820, a more uniform low amplitude wavefront can be provided as illustrated in FIG. 17A. Faint diagonal rays point to four lead conductor induced errors being limited to sub-wavelength retardation and therefore to low aberrations. It is noted that the internal annular ring control electrode 820 can be located much closer to the interior edge of the hole patterned electrode 814 (transparent ITO) providing an increased clear aperture. Without limiting the invention, FIG. 16 illustrates a layered geometry wherein the hole patterned electrode is not interrupted and the lead conductors 850 for the inner donut ring electrode 820 are provided on a different layer electrically separated by an isolator 870.

Figure 17B:
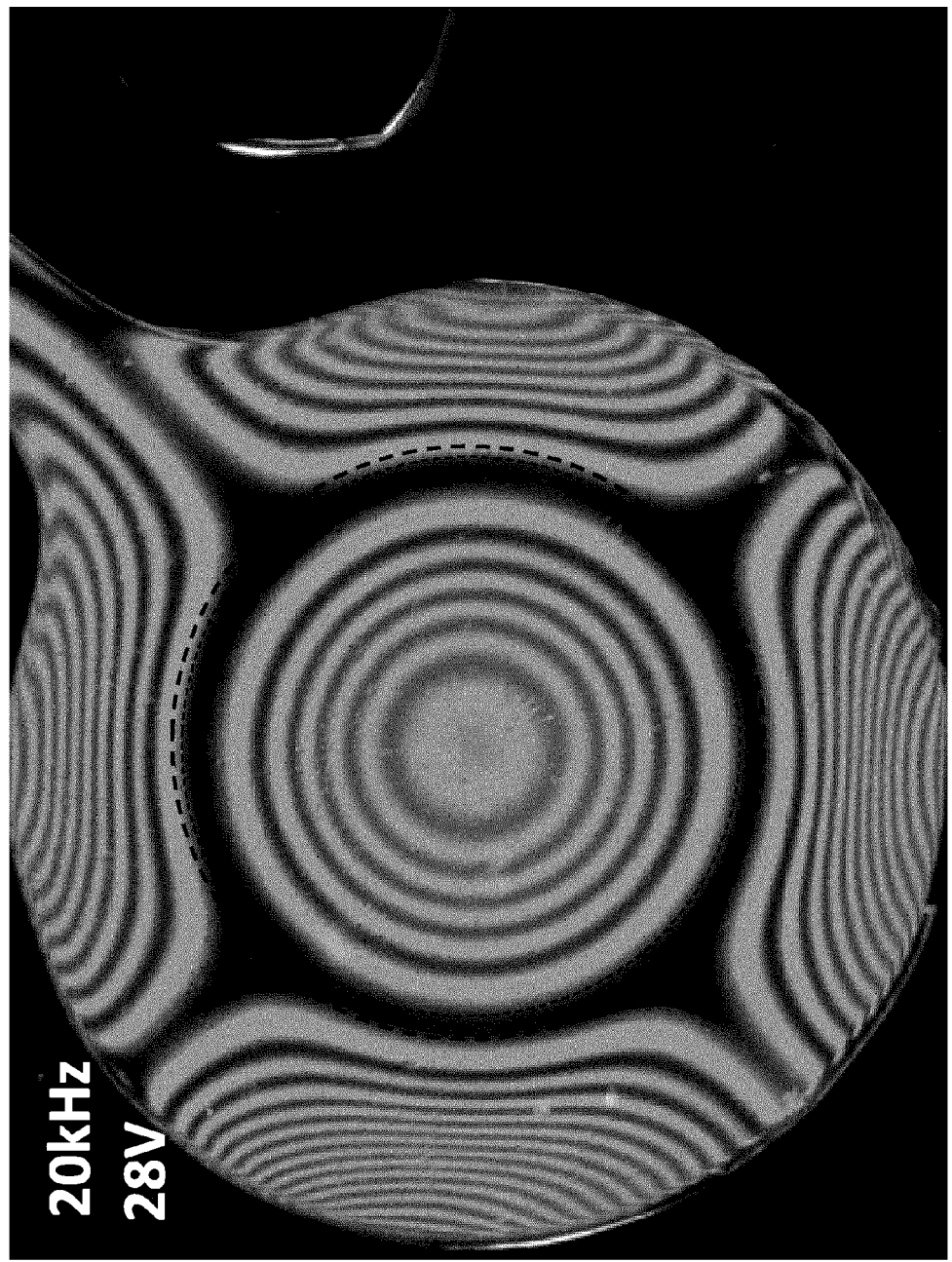

FIG. 17B illustrates the wavefront adjustment provided by a 20 kHz drive signal having an amplitude of 28V. Advantageously, the wavefront adjustment provided is more symmetric with substantially all lead conductor induced distortions outside the diameter of the hole patterned control electrode 814, thereby providing an increased clear aperture. Such lead conductor induced distortions can be masked by a non-transparent hole patterned electrode 814.

Figure 18A:
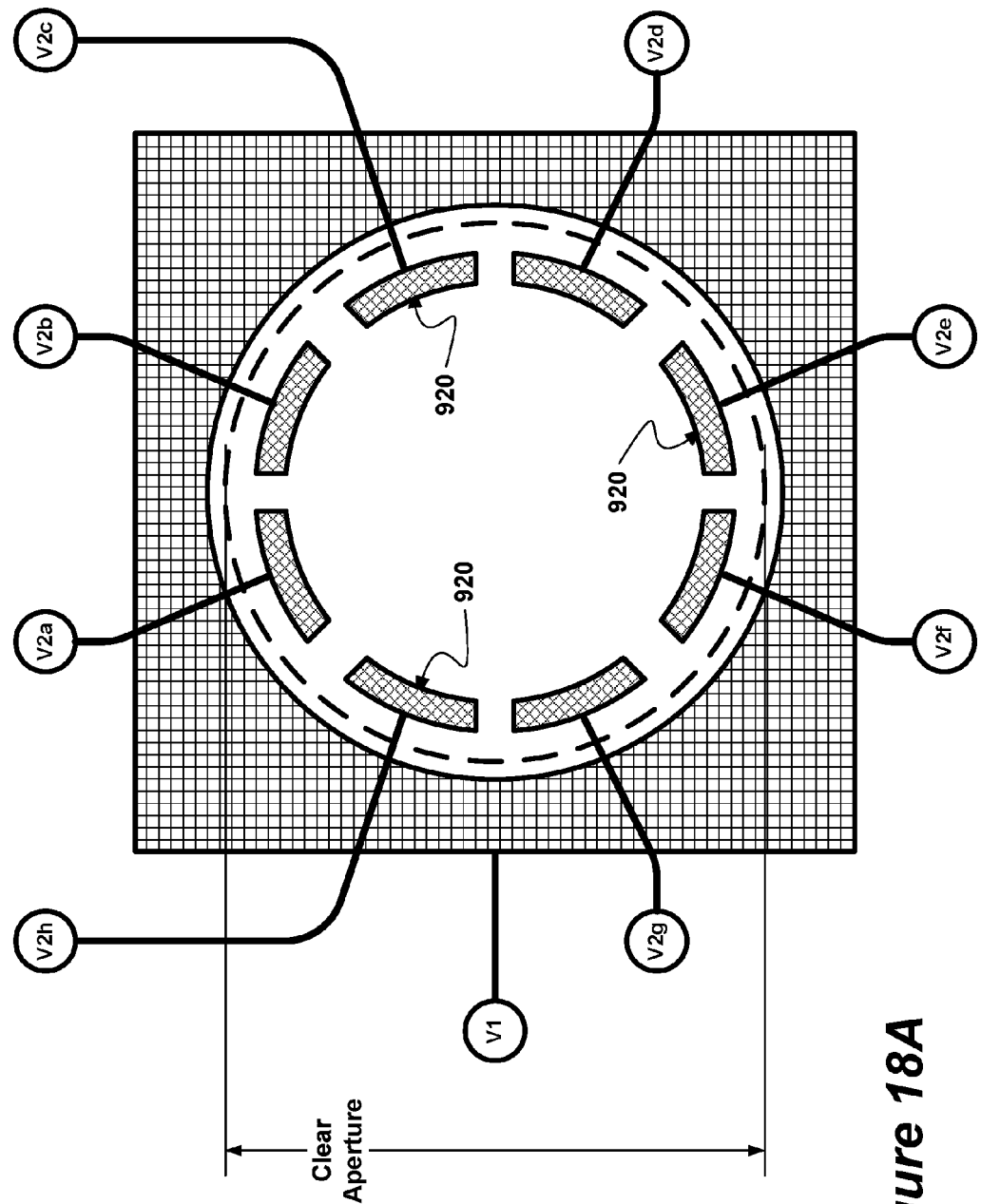
FIGS. 18A and 18B are diagrams illustrating top plan views of liquid crystal lenses in accordance with other implementations of the proposed solution.

While some of the liquid crystal cells described above, and illustrated in the drawings, have an integral hole-patterned electrode, the invention is not limited thereto. For example, International PCT Application PCT/CA2010/002023 filed Dec. 23, 2010, which is incorporated herein by reference, describes TLC optical devices, including but not limited to lenses, having a segmented hole-patterned electrode for controlling the electric field across the liquid crystal layer, expressly enabling asymmetric phase profiles to be applied for image tilting, optical image stabilization and sub-pixel shift capability. With feedback from an image sensor, such geometry can be used for image stabilization. Advantageously, the segmented geometry as described in the related PCT/CA2010/002023 International PCT Application, which is incorporated herein by reference, can be employed, with the auxiliary control elements described therein, to remove focus tilt, astigmatism, comma, etc. manufacturing errors. Herein "interrupted" is employed when a single drive signal is employed with the hole patterned electrode 814, and "segmented" when allowance is made for applying different drive signals to individual hole patterned electrode segments:

FIG. 18A illustrates another implementation of the proposed solution wherein the hole patterned electrode 814 is not segmented while the internal donut ring control electrode 920 is segmented providing both wavefront adjustment towards sphericity and correction of manufacturing/assembly errors. Without limiting the invention, the lead conductors applying $V_2$ drive signals to each segment are illustrated out of plane as in FIG. 16.

Figure 18B:
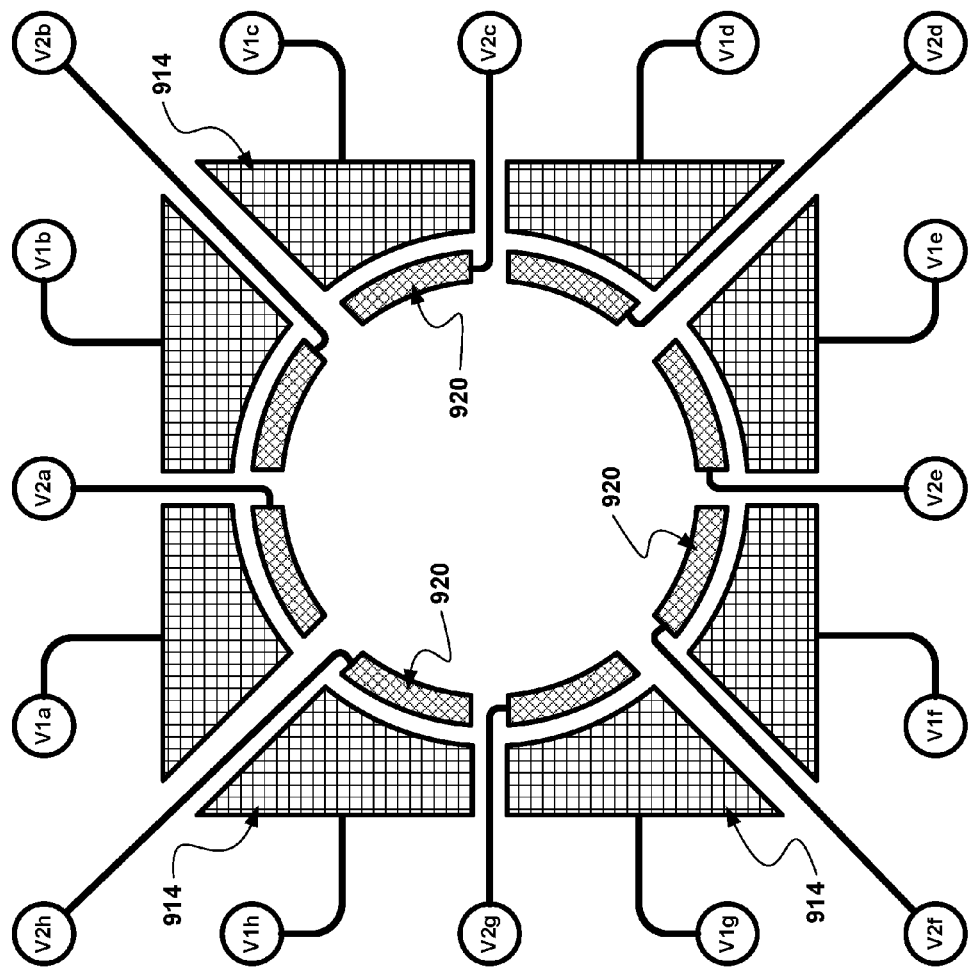

FIG. 18B illustrates a top plan view of the liquid crystal lens of FIG. 16, in accordance with another implementation of the proposed solution. The hole patterned electrode 914 illustrated has a segmented geometry as described in the related PCT/CA2010/002023 International PCT Application, which is incorporated herein by reference, and can be employed, with the auxiliary control elements described therein, to remove undesirable focus tilt, astigmatism, comma, etc. stemming from manufacturing errors. The multiple lead conductors applying $V_2$ to segments of the inner donut ring control electrode 920 can be wafer manufactured (deposited) in the same plane with the inner donut ring control electrode 920 and the segments of the hole patterned control electrode 914.

It can be appreciated that the desirable optical power variations presented in FIGS. 14, 15B, 15C and 17B are obtained using the geometries presented in FIGS. 12, 13 and 16, respectively, by employing operational voltages in the range of 28V (see FIG. 17B). This is due to the geometries employed wherein the external control ring electrode 814, the internal ring electrode 820 and the WCL 819 are 'one substrate 211 away' from the LC layer 210 being controlled. In contrast, in geometries presented in FIGS. 2, 4 7B and 7C, the external control ring electrode 214/714, the internal ring electrode 20/420 and the WCL 219 are substantially adjacent to the controlled LC layer 210, and lower voltage operation closer to 5V is possible. This is important for TLCL employed in battery operated portable devices.

Figure 19:
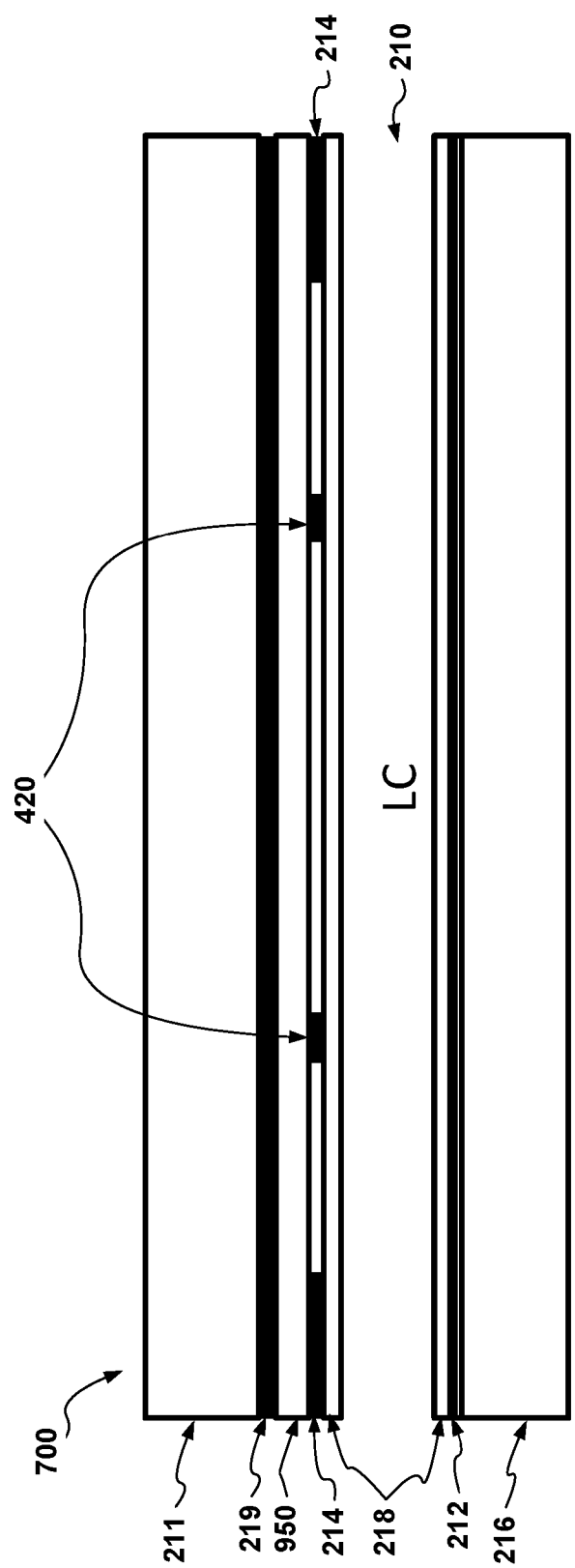
FIG. 19 is a schematic diagram illustrating another half tunable lens geometry in accordance with the proposed solution.
Figure 20:
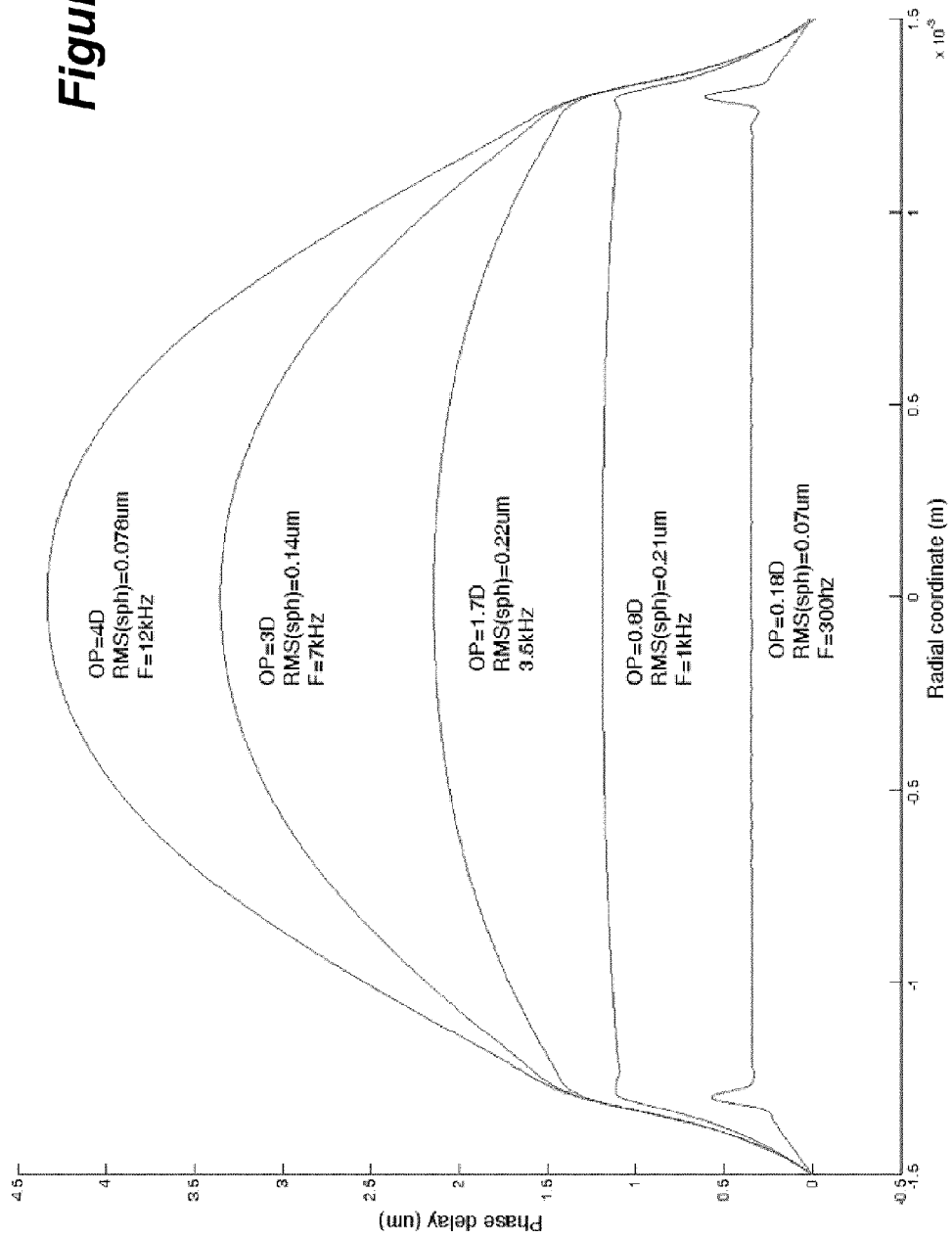
FIG. 20 is a schematic graph illustrating optical power variation across the aperture for the geometry illustrated in FIG. 20.

FIG. 19 illustrates, in accordance with the proposed solution, a polarization dependent half TLCL geometry 700 employing an inner control ring electrode 420 in which the external control ring electrode 214, the internal ring electrode 420 and the WCL 219 are substantially adjacent to the LC layer 210. Other features of the geometry include an insulating material, such as SiO2, separating layer 950 between the external control ring electrode 214 and the internal ring electrode 420, and the WCL 219. FIG. 20 illustrates a graph of the phase delay variation with the radial dimension of the TLCL for different optical powers. Notably while the clear aperture is larger, increasing the clear aperture further is limited by optical power variation peripheral discontinuities at low optical powers. This is the case in FIG. 20 where optical power modulation is achieved with frequency control without any corresponding voltage control.

Figure 21:
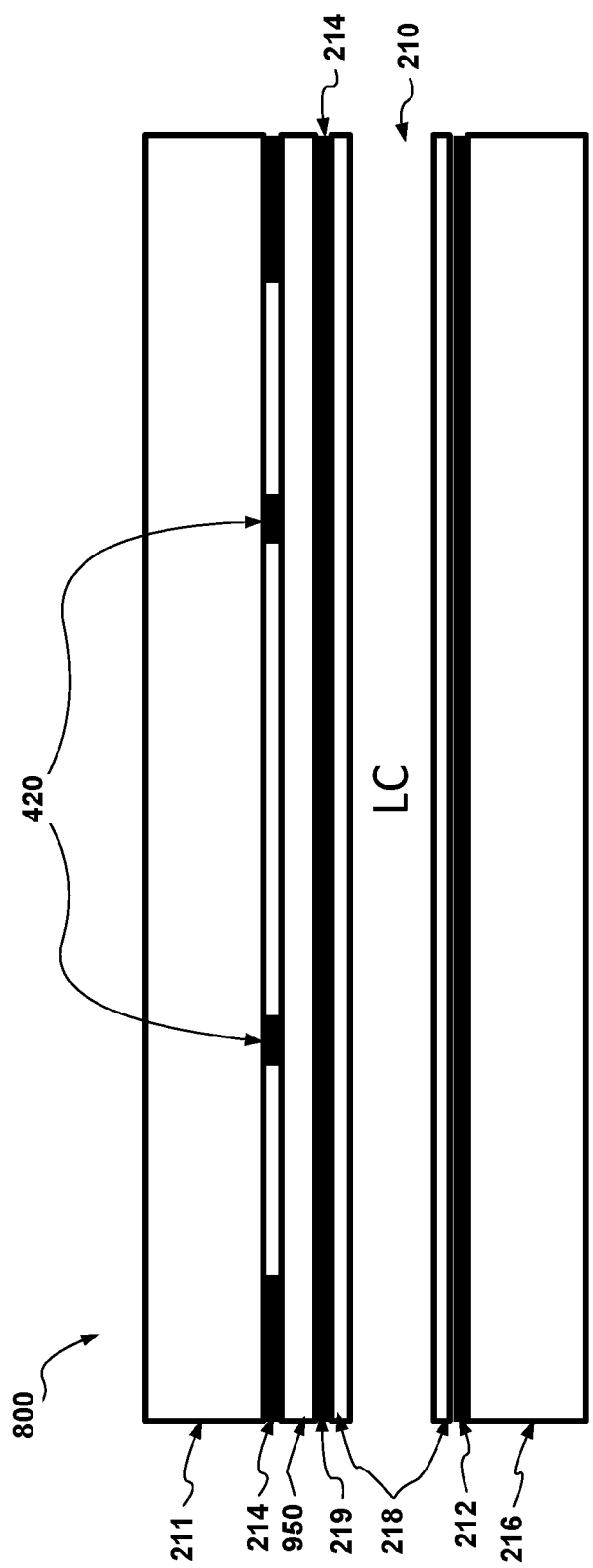
FIG. 21 is a schematic diagram illustrating a further half tunable lens geometry in accordance with the proposed solution.
Figure 22:
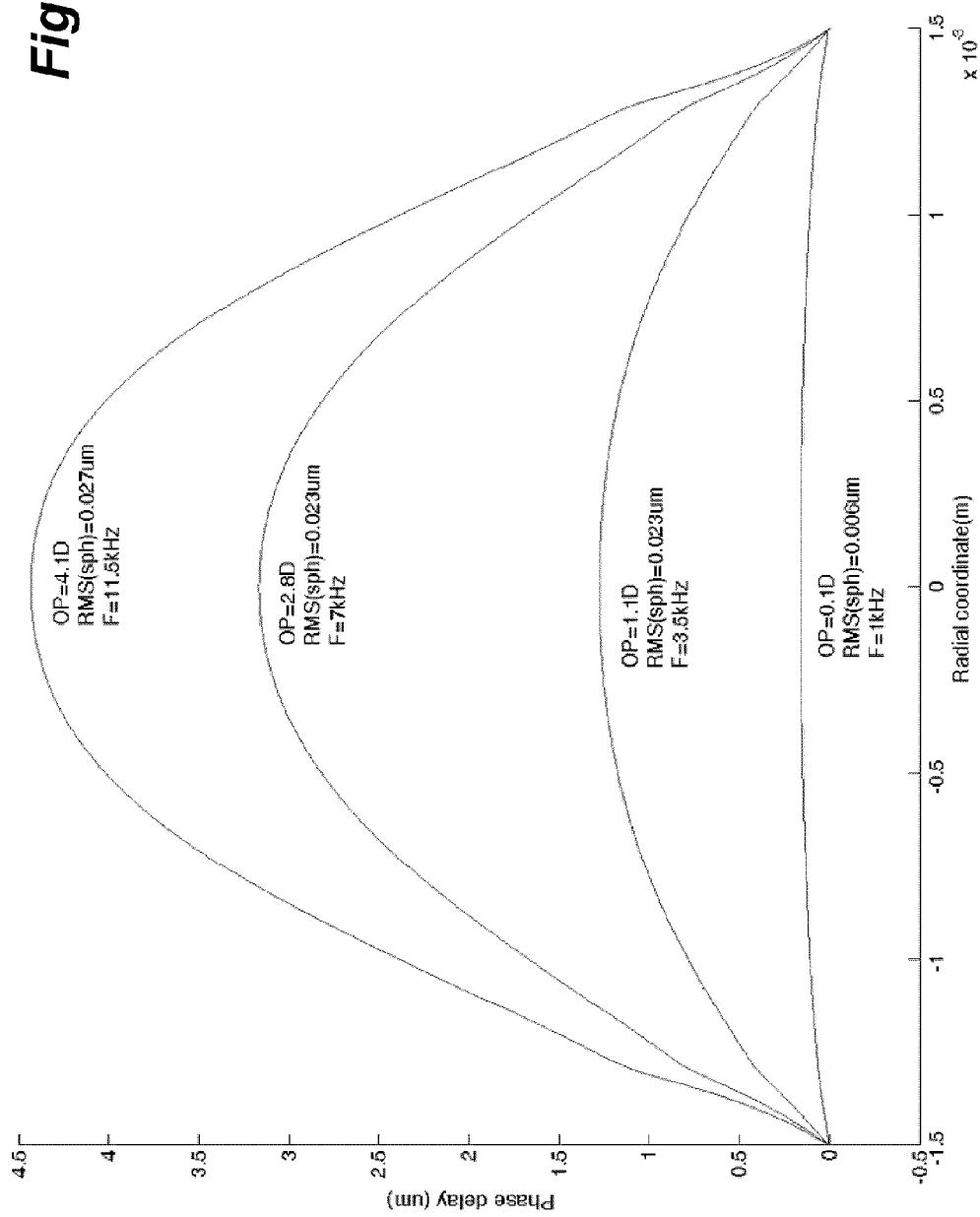
FIG. 22 is a schematic graph illustrating optical power variation across the aperture for the geometry illustrated in FIG. 22.

FIG. 21 illustrates, in accordance with the proposed solution, a polarization dependent half TLCL geometry 800 employing the external control ring electrode 214 and the internal ring electrode 420 in reverse layer order with the WCL 219. This, has been discovered, reduces the peripheral optical power discontinuities as illustrated corresponding FIG. 22. Notably, this increase in clear aperture is achieved at lower operational voltages.

Schmidt Corrector Plate

Not all aberrations and image distortions produced in an (complex/compound) optical system can be compensated for with a segmented electrode structure. For example, some distortions have a patterned aspherical character due to the fact that (bulk material) glass lenses have a varying material size throughout. One such distortion is caused by the optical rays passing through different thickness concentric portions of an optical element to focus at different focus distances. Such distortions are corrected by a Schmidt corrector plate.

Figure 23:
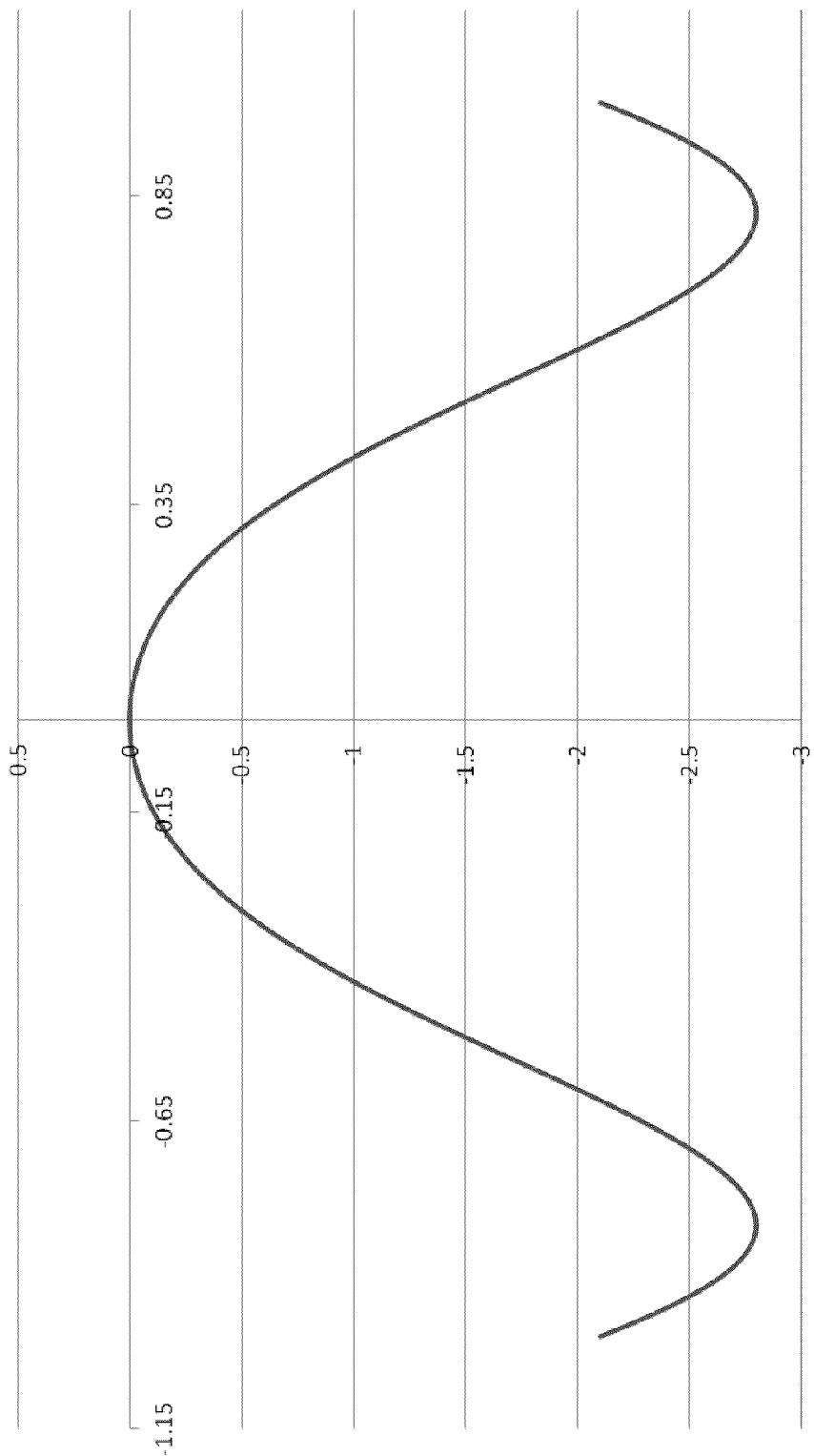
FIG. 23 is a schematic graph illustrating an electric field distribution across the aperture of an optical device produced by a donut shaped control electrode alone in accordance with the proposed solution.

In accordance with another embodiment of the proposed solution, the internal 420 and external 714 control ring electrodes of the geometry illustrated in FIGS. 7A to 7C are electrically connected, that is $V_1=V_2$ without the floating electrode 430. The electrical field generated by applying a single control drive signal to both internal 420 and external 714 ring control electrodes is illustrated in FIG. 23 resembling a sombrero as described herein below. FIG. 23 is a normalized graph of the electric field variation.

Figure 24:
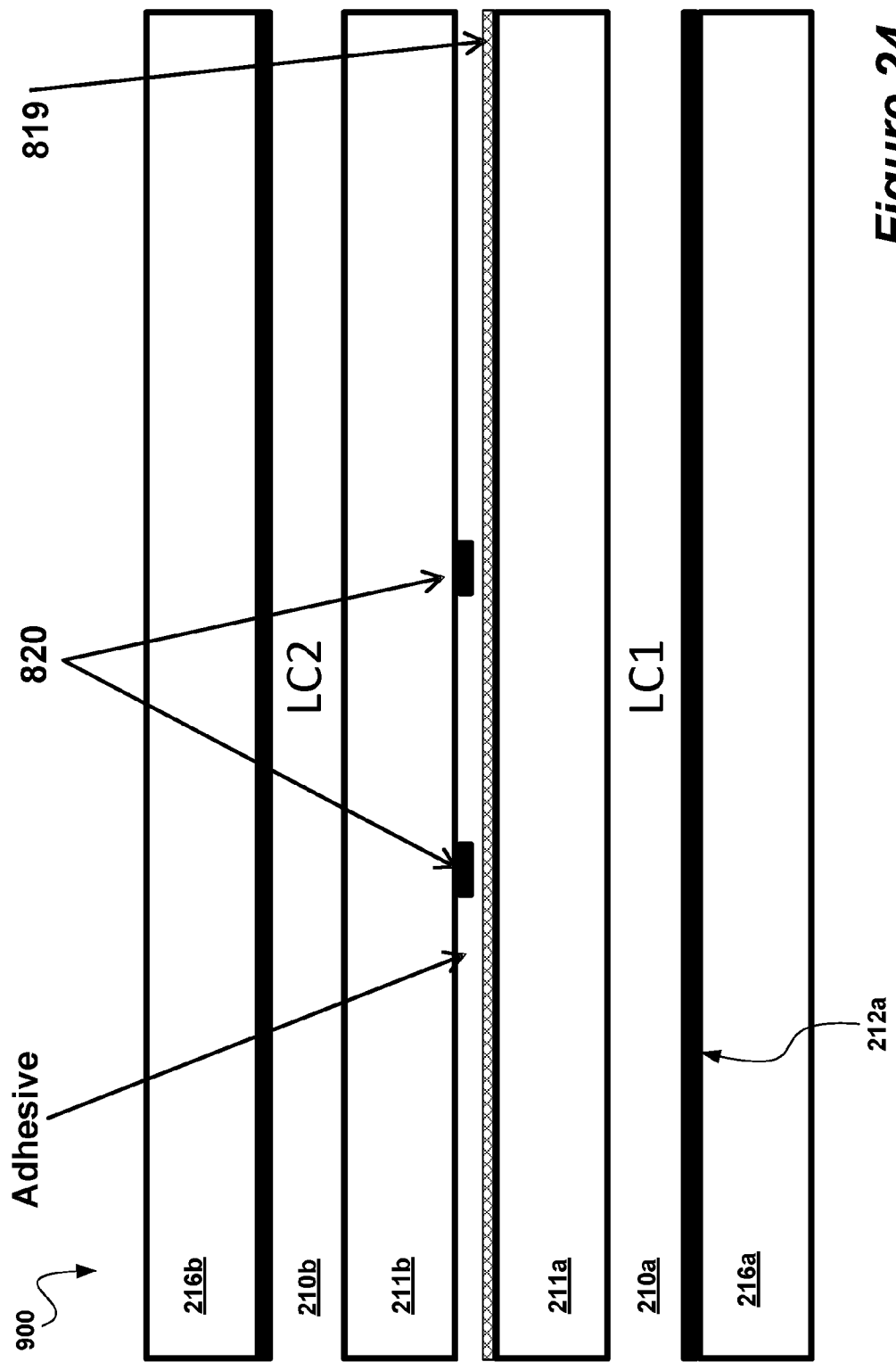
FIG. 24 is a schematic diagram illustrating a polarization independent layered optical device structure employing an single donut ring shaped control electrode and a single weakly conductive layer to synchronously operate two LC cells, in accordance with the proposed solution.

In accordance with another embodiment of the proposed solution, FIG. 24 illustrates a modified polarization independent optical device layered structure 900 based on the layered structure illustrated in FIG. 12 without the hole patterned electrode 814. The electric field generated by the donut ring shaped electric field control electrode 820 is also illustrated in FIG. 23 and resembles a sombrero. When employed in a TLCL optical device this demonstrates the influence of a transparent annular ring shaped electrode 820 on the electric field and therefore on the wavefront adjustment. Such a TLCL optical device can be configured as a Schmidt-like corrector plate for an optical system. In accordance with the proposed solution, such a wafer scale produced Schmidt-like corrector plate can be further configured to provide an adjustable correction. While not shown, a drive signal can be applied to the transparent donut ring shaped control electrode 820 (inner with respect to the clear aperture) via one, preferably more, transparent lead conductor(s). The invention is not limited to a contiguous donut ring shaped control electrode 820, the donut ring shaped control electrode 820 can be segmented to provide a Schmidt-like corrector plate and also to correct for aberrations for example, manufacturing errors, assembly inaccuracies, temperature compensation, etc. as mentioned herein, wherein each segment can be individually/independently driven.

Central Wavefront Adjustment Profile Improvement

Figure 1:
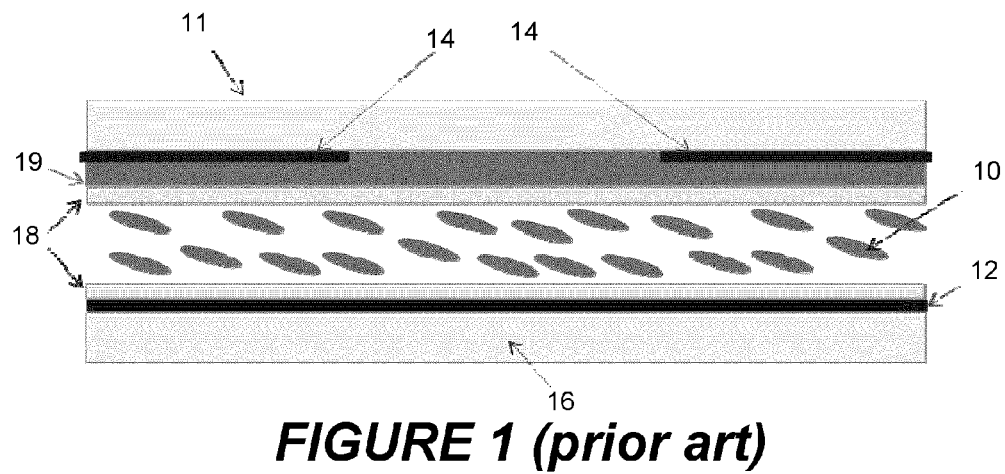
FIG. 1 is a schematic representation of a prior art LC lens using a hole-patterned electrode with "modal control"
Figure 3:
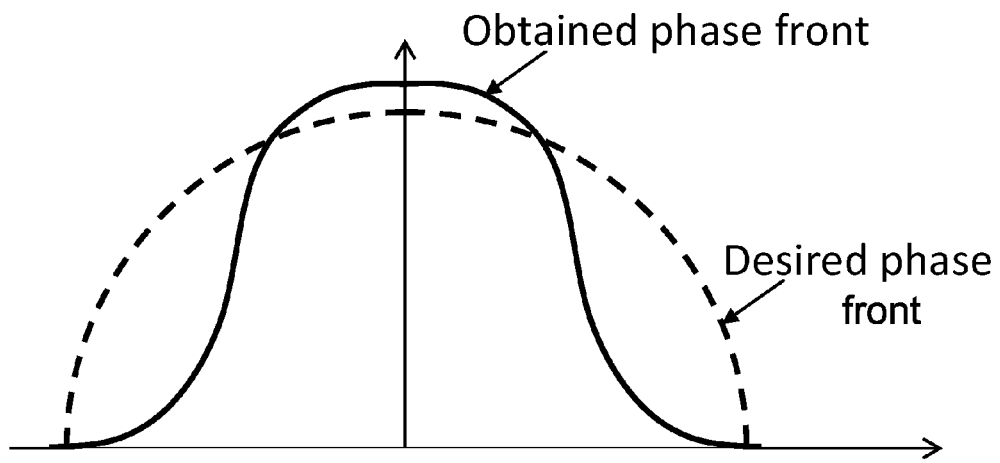
FIG. 3 is a schematic diagram illustrating, in exaggerated fashion, aspherical wavefront distortions as generated by a hole patterned ring electrode and a weakly conductive layer, and an example (among others) of a desired wavefront form.

In accordance with another embodiment of the proposed solution, at least one electrically floating electrode or multiple electrically floating electrode structures each generally having an obround, hole patterned, tape, etc. shape can be employed in a LC optical device to provide a wavefront profile correction. For LC lens optical devices, at least one floating electrode or multiple floating electrode structures each having a disc, ring, donut, etc. shape can be employed to reshape the wavefront otherwise generated by the electric field control structure combination of the hole patterned electrode and weakly conductive layer to provide wavefront profile correction towards spherical wavefront adjustment. For a TLCL, the sphericity of the wavefront adjustment can be improved as illustrated in FIG. 3 in dashed line particularly in the center.

Figure 25A:
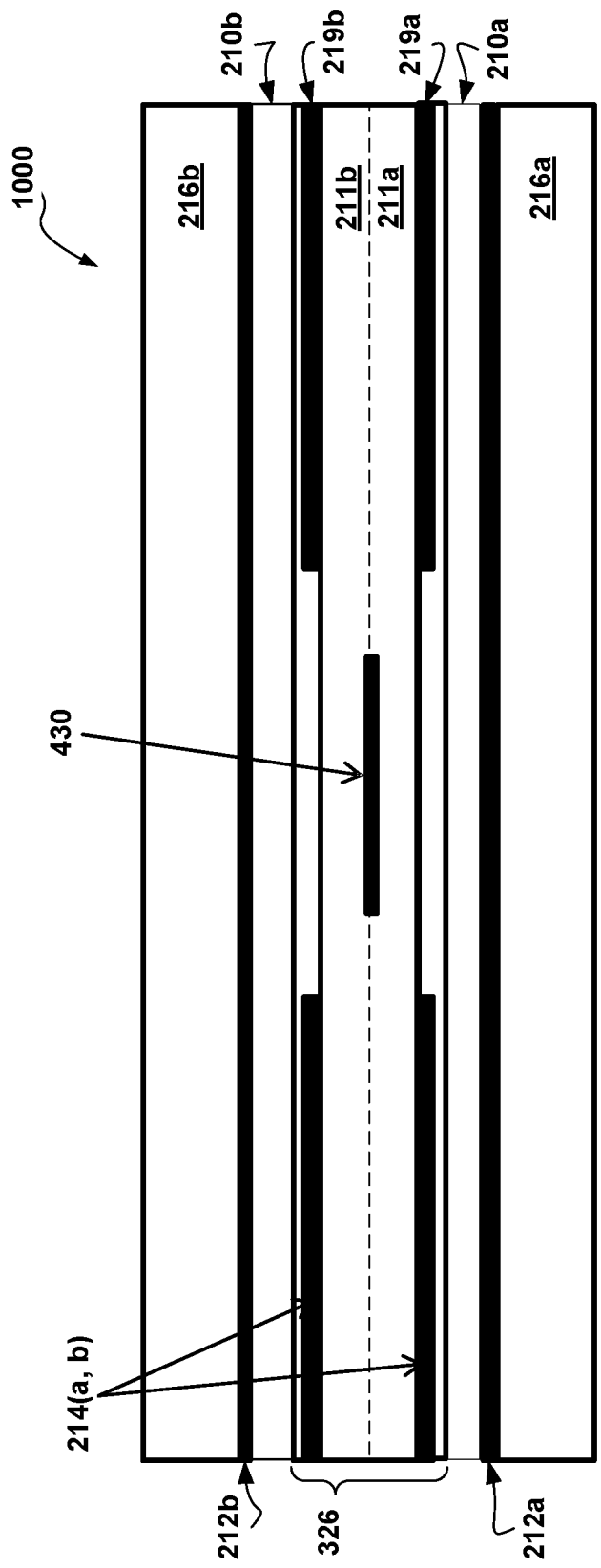
FIG. 25A is a schematic diagram illustrating a cross-sectional view of a liquid crystal lens, in accordance with one implementation of the proposed solution, with two LC cells having two weakly conductive layers and a common floating electrode in a shared common substrate.

In accordance with an implementation of the proposed solution, FIG. 25A illustrates an electrically floating, i.e. not electrically connected, disc-shaped layer (430) between two WCL layers 219(a, b) of a full TLCL structure 1000. Preferably the floating layer (430) is non-dielectric in composition, including conductor or semiconductor materials, and as such can be an electrically un-driven electrode 430 which changes the wavefront phase profile towards a desired spherical phase profile. Disc shaped floating electrodes 430 tend to have an effect (in cross-section) in the central part of the electric field, which as mentioned hereinabove is flattened for a hole patterned electrode 214(a, b). The floating electrode 430 being positioned between the two LC half-lenses provides synchronized operation of the combined full TLCL by generating phase front profile adjustments in each half-lens.

Generally, as floating electrodes are located along the optical path within the hole patterned electrode 214(a, b) opening, and possibly within the diameter of the clear aperture of a TLCL, the floating electrodes 430 are preferably transparent. However, in some implementations the floating electrode can also participate in defining the optical aperture of the overall optical device, in which case the floating electrode 430 may not be wholly transparent.

From a manufacturing perspective, FIG. 25A illustrates a full TLCL polarization independent geometry wherein the mid substrate 326 is implemented as two separate substrates 211a/211b on at least one of which the floating electrode 430 is deposited. The invention is not limited to same thickness separate mid substrates making up the mid substrate 326. The invention is also not limited to depositing the floating electrode 430 between the separate mid substrates 211(a, b) of an LC lens optical device. Floating electrodes 430 can be deposited on each side of a single mid substrate 211 either in contact or not in contact with the WCL 219(a, b) layer on that corresponding side of the mid substrate 211 to provide the operational wavefront adjustment effect sought in the overall TLCL optical device.

Figure 25B:
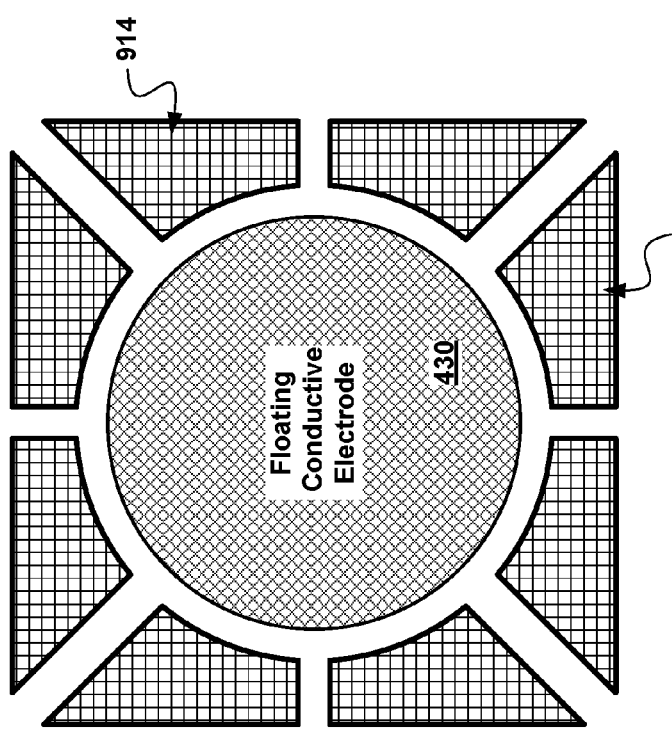
FIG. 25B is a schematic diagram illustrating a top plan view of the liquid crystal lens of FIG. 25A, in accordance with another implementation of the proposed solution.

FIG. 25B illustrates a top plan view of the liquid crystal lens of FIG. 25A, in accordance with another implementation of the proposed solution. The external hole patterned electrode 914 illustrated in FIG. 25B has a segmented geometry as described in the related PCT/CA2010/002023 International PCT Application, which is incorporated herein by reference, and can be employed, with the auxiliary control elements described therein, to also remove focus tilt, astigmatism, comma, etc. manufacturing errors.

Figure 26:
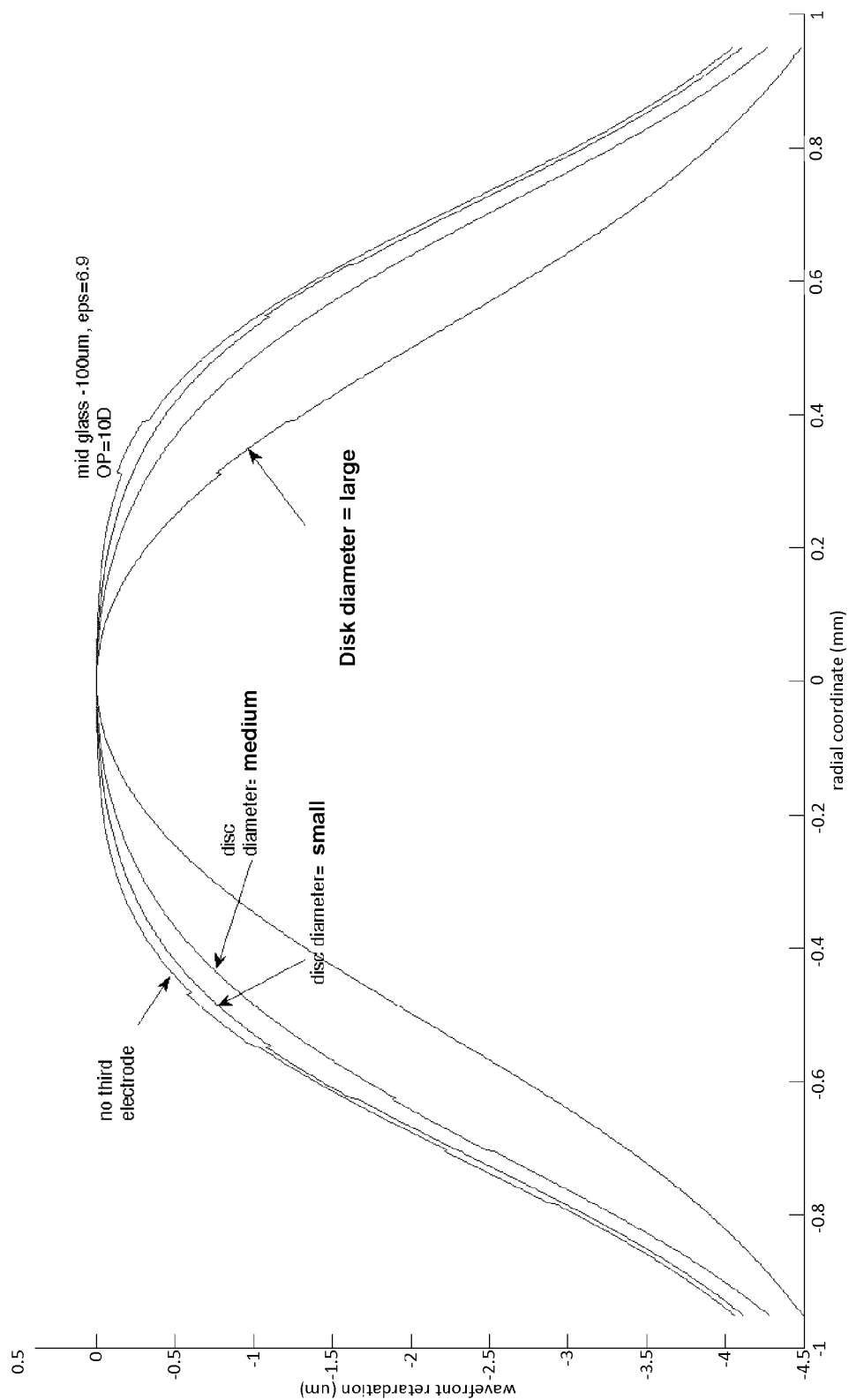
FIG. 26 is a graph illustrating theoretical wavefront adjustment in a LC lens having a layered geometry as illustrated in FIG. 25 by employing a conductive disc floating electrode in accordance with the proposed solution.

FIG. 26 graphically illustrates wavefront adjustment in a LC lens employing a conductive disc floating electrode 430 in a layered geometry illustrated in FIG. 25A. The curve labeled "no third electrode" corresponds to layer geometries, without a floating electrode 430 present, providing a wavefront profile having a flat region in the center which can lead to relatively high spherical aberrations. With the addition of a floating electrode 430, for example a disc of ITO, the wavefront profile becomes more and more spherical in the center with an increase in the diameter of the floating electrode 430. Ultimately the wavefront adjustment profile improvement corresponding to a diameter of the floating disc electrode 430 approaching the diameter of the hole patterned ring-shaped electrode 214 as illustrated by the curve labeled 'large disk diameter'.

Figure 27:
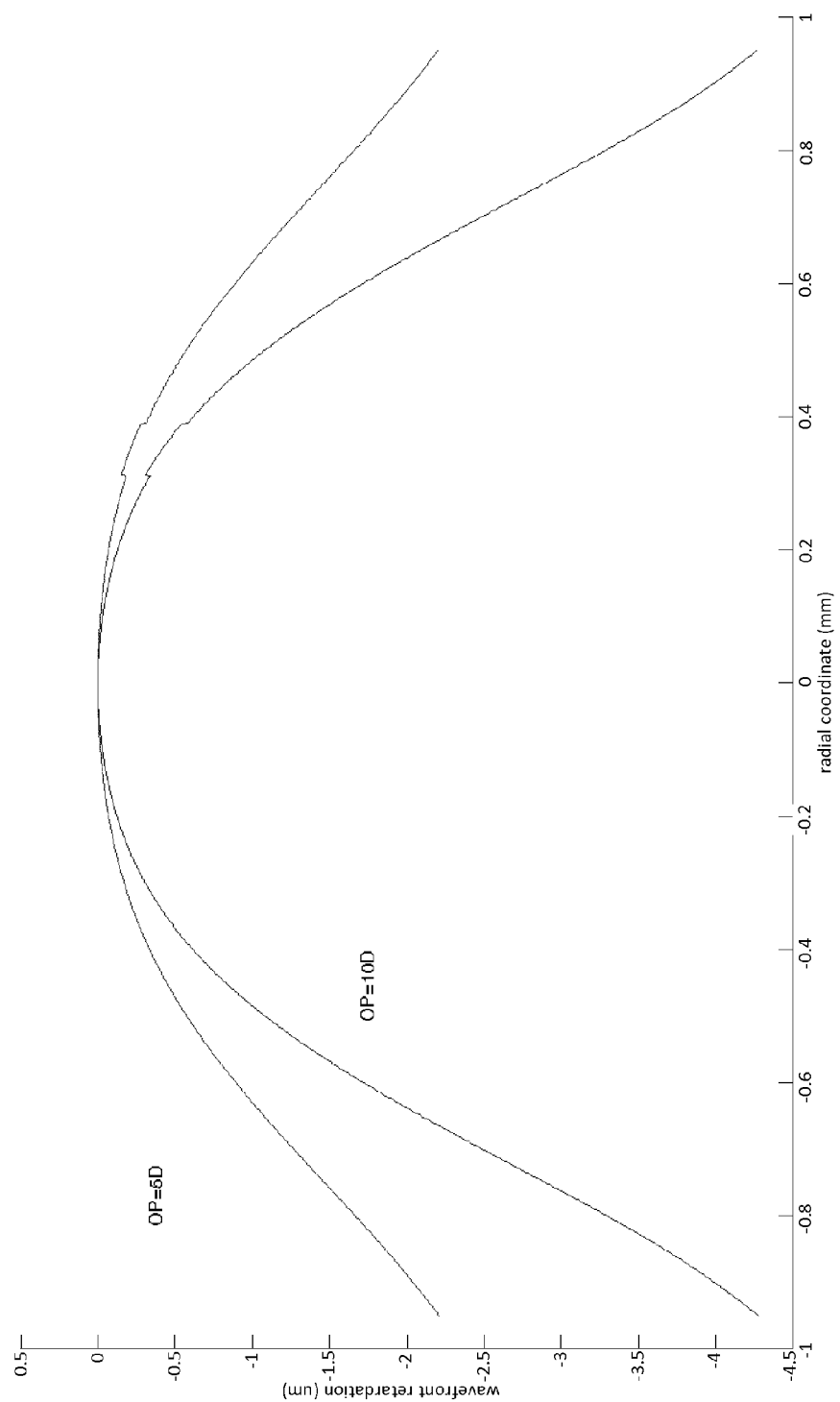
FIG. 27 is a graph illustrating, in accordance with the proposed solution, circularization of the wavefront profile improvement being retained at other optical power settings employing the same disc shaped floating electrode.

The geometry of the floating electrode 430 can be configured for different optical device parameters (including parameters relating to camera formats in which the TLCL is used) such as, but not limited to: mid substrate thickness, clear aperture, gap material dielectric constant, etc. The general tendencies are similar, with some quantitative differences, which can be taken into account for each LC lens. FIG. 27 illustrates measured circularization (in cross-section) of the wavefront adjustment profile improvement provided by a disc shaped floating electrode being retained at different optical power settings for example at 5 diopters and 10 diopters.

The invention is not limited to a disk shaped floating conductive electrode 430 employed in a TLCL optical device. For example, an elongated floating conductive electrode can be employed in order to induce or correct astigmatism. For certainty, an elongated floating conductive electrode can be employed in a cylindrical lens where the geometries illustrated in FIGS. 25A, 26 and 27 represent cross-sections perpendicular to the length of such cylindrical lens.

Figure 28:
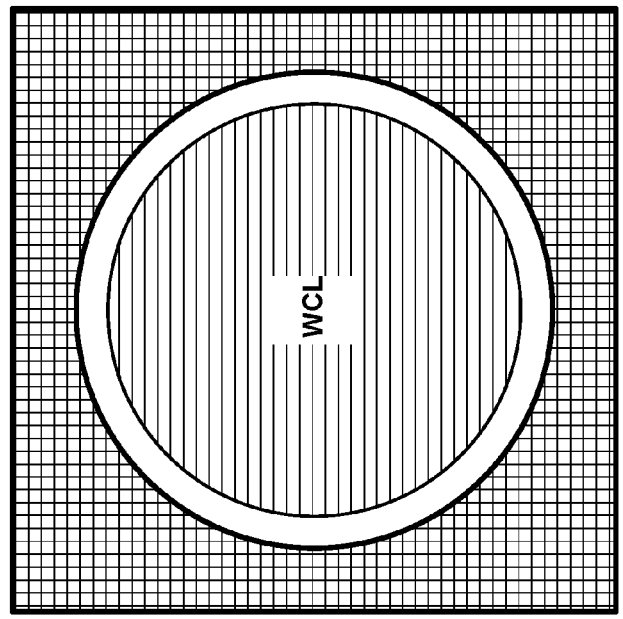
FIG. 28 is a schematic diagram illustrating cross-sectional view of a liquid crystal lens, in accordance with a further implementation of the proposed solution, with two LC cells and a middle weakly conductive layer of limited extent in a shared common substrate.

In accordance with a further implementation of the proposed solution illustrated in FIG. 28, it has been discovered that a single weakly conductive material layer replacing the floating conductive electrode of FIG. 25A, however without weakly conductive material across the hole patterned electrodes 214(a, b), can be employed to improve sphericity in the central portion of the aperture substantially as illustrated in FIGS. 26 and 27.

Extension to Larger Optical Device System

Figure 29:
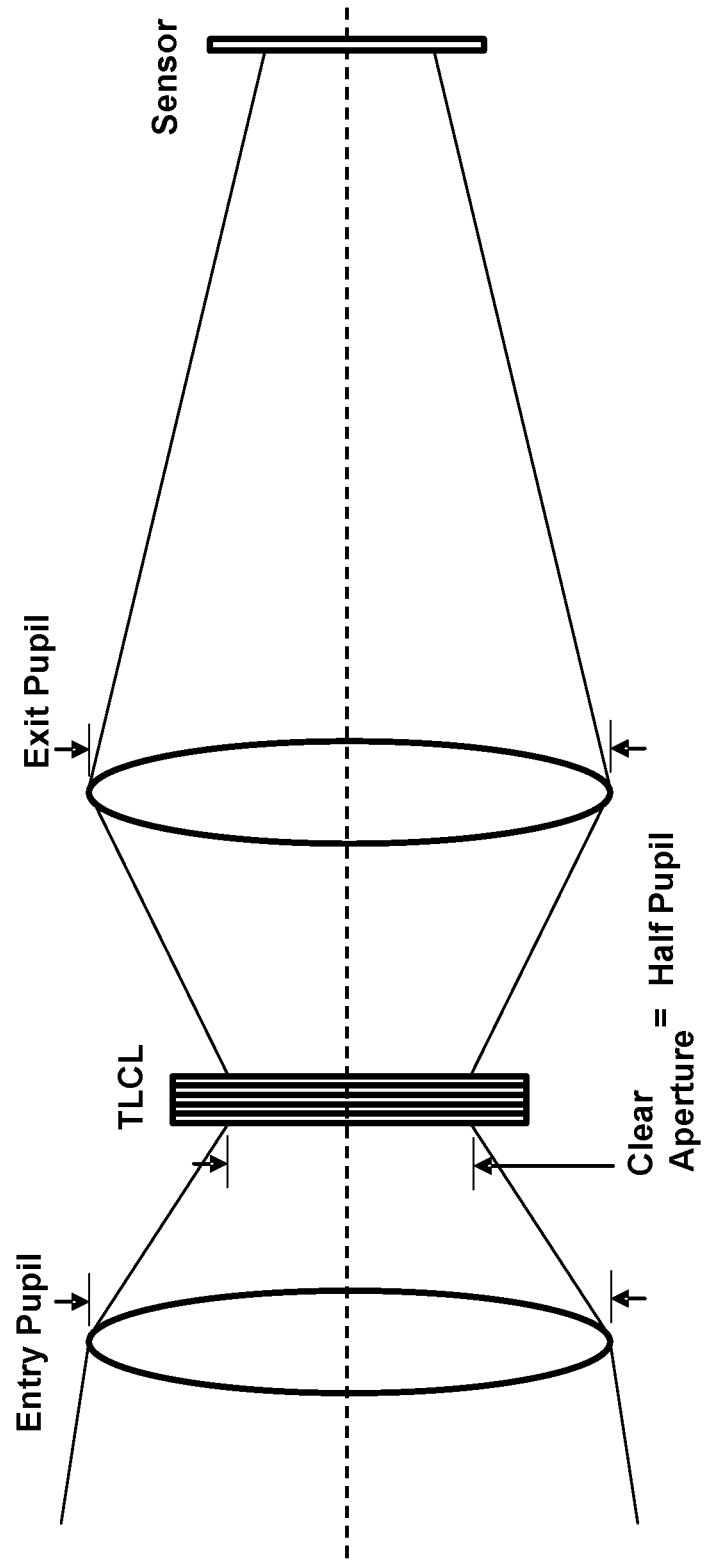
FIG. 29 is a diagram illustrating the use of a tunable liquid crystal lens in a larger system provide an increased optical aperture in accordance the proposed solution

One important parameter of the above tunable liquid crystal optical devices, and in particular important to TLCLs is the clear aperture. In the above examples, achieving a 3 mm aperture has been demonstrated with very low aberrations. The reduced aberrations provided enable the use of such a TLCL to provide optical power adjustment for optical systems having larger apertures. For example FIG. 29 illustrates the use of a TLCL having a geometry substantially similar to that illustrated in FIG. 4 in an optical system having an aperture twice the size. Front and back optical elements, schematically illustrated by ideal lenses respectively having entry and exit pupils, double the size of the clear aperture of the TLCL by respectively compressing and expanding, the incident light beam to adapt the incident beam size to pass through the clear aperture of the TLCL optical element. The TLCL can then be employed to focus an image onto the optical sensor behind the overall optical system as illustrated in FIG. 29. For certainty, it will be appreciated that the optical system illustrated in FIG. 29 is highly schematic and that a multitude of other optical systems can be configured to employ a TLCL as a motionless adaptive optical element, for example to provide focus or another adaptive optical function.

It is understood that larger optical systems such as the one schematically illustrated in FIG. 29 does not employ ideal optical elements. Such other optical elements can themselves have manufacturing defects introducing aberrations or introduce aberrations due to assembly imprecision. In accordance with the proposed solution, the TLCL can be configured to compensate for such aberrations.

Intraocular Device Application

Figure 30:
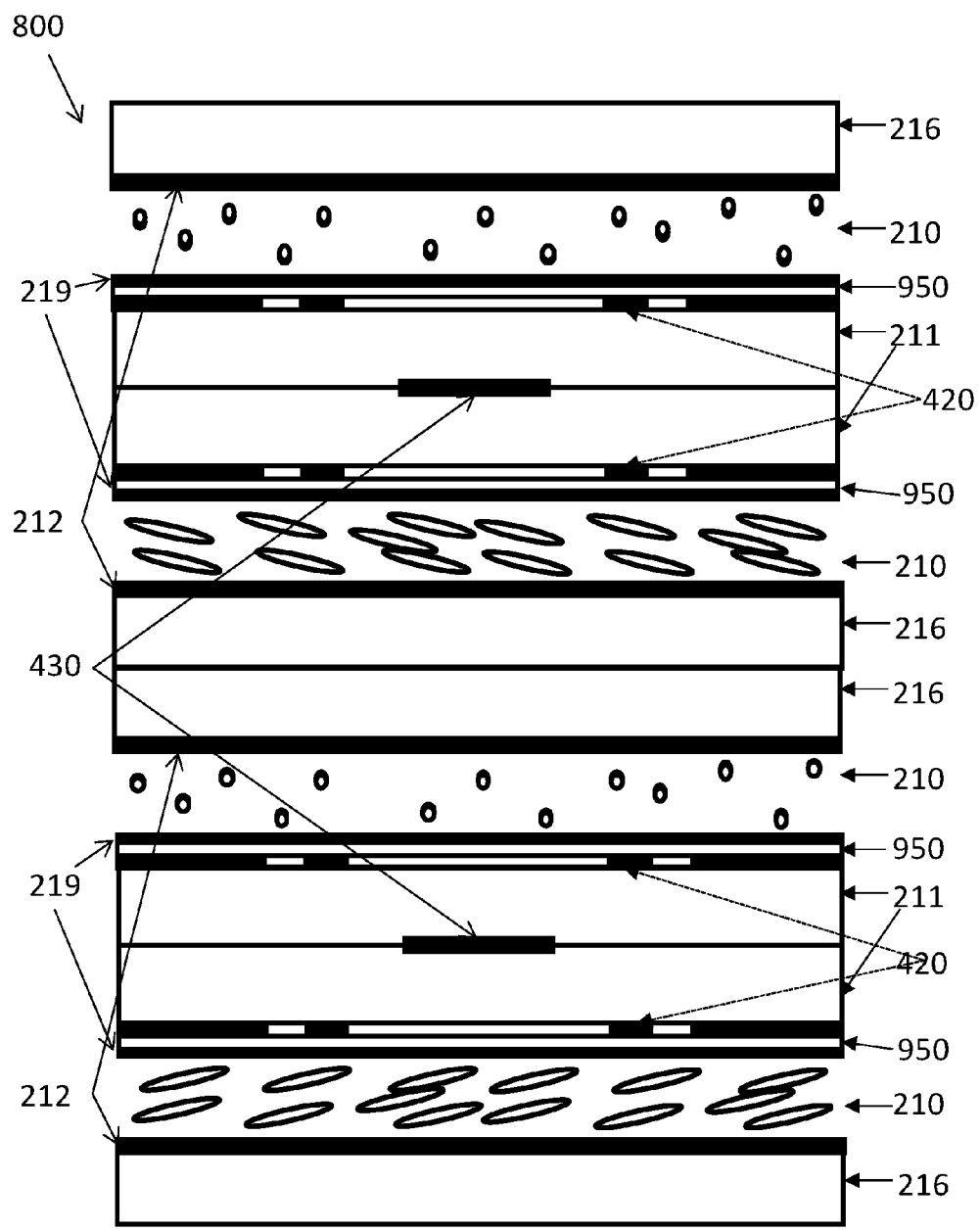
FIG. 30 is a schematic diagram illustrating another embodiment of the proposed solution.
Figure 31:
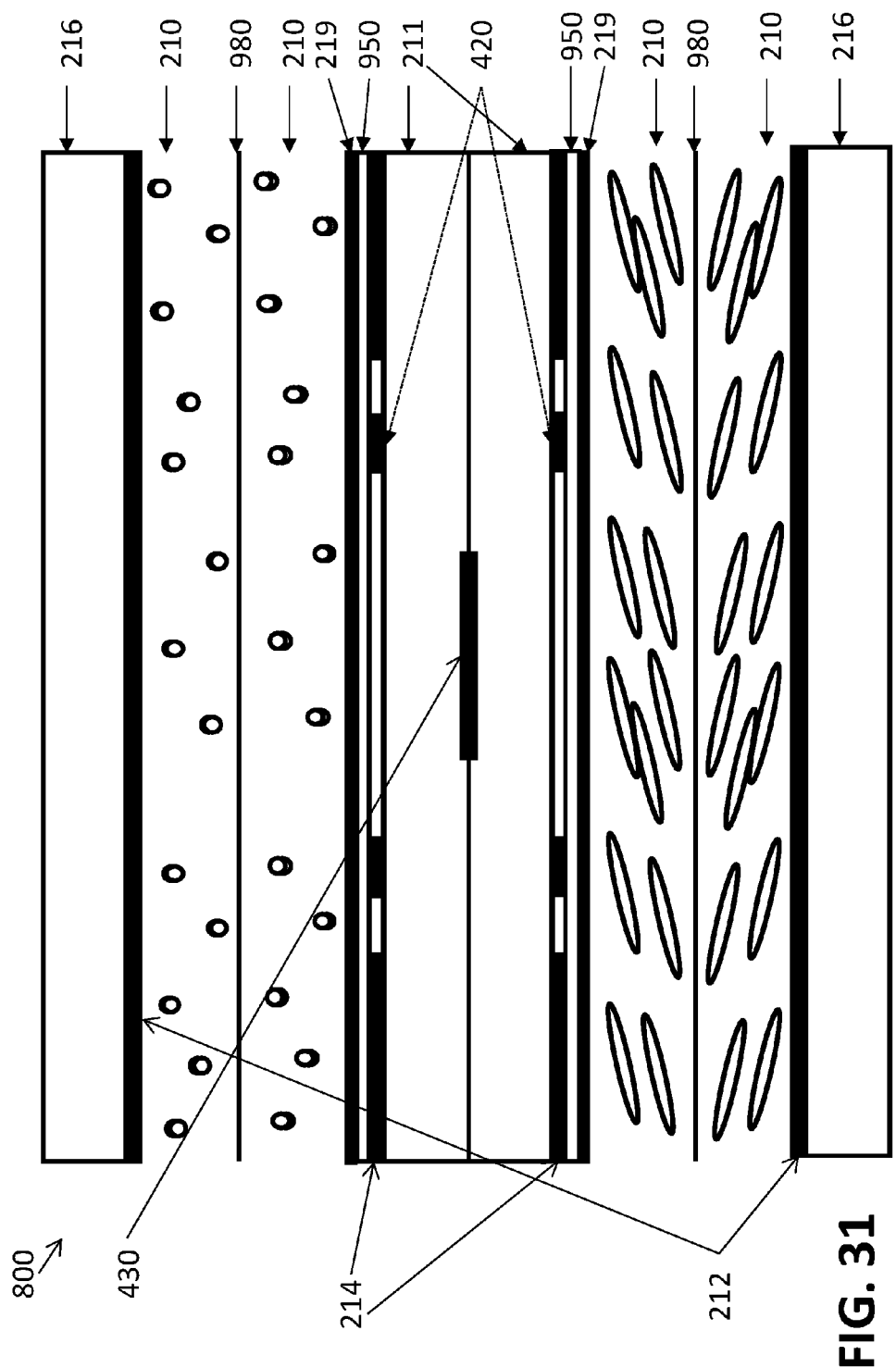
FIG. 31 is a schematic diagram illustrating a further embodiment of the proposed solution.

In accordance with another embodiment of the proposed solution FIG. 30 illustrates a dual full LC lens structure 800 employing two full LC lenses, without limiting the invention, for example each having the layer geometry illustrated in FIG. 21 herein wherein corresponding LC layers 210 in each full LC lens have directors oriented in opposing directions. Besides providing double the optical power of each full LC lens, the overall geometry also provides a reduction in image splitting between the two polarizations of light as described in U.S. patent application Ser. No. 12/996,593 filed 2010-12-06 claiming priority from U.S. Provisional Patent Application 61/074,651 filed 2008 Jun. 6, the entireties of which are incorporated herein by reference. While the LC lens geometry illustrated in FIG. 30 includes dual LC lenses doubling the thickness of the layered geometry, a reduction in the overall layered geometry is possible as illustrated in FIG. 31. The full LC lens layered geometry 800 illustrated in FIG. 31 employs the same electrode structure as illustrated, for example, in FIG. 21 to drive dual adjacent LC layers 212 with LC directors oriented in opposing directors. A rubbed or stretched membrane 980 is employed as an alignment layer in between adjacent LC layers 210. In accordance with yet another embodiment of the proposed solution, the reduction in image splitting can also be achieved by shifting each half LC lens in a full LC lens geometry, for example, as illustrated in FIG. 21 to counteract image shifts between the two polarizations as described in U.S. Provisional Patent Application 61/800,620 filed 2013 Mar. 15, which is incorporated herein by reference.

Figure 32:
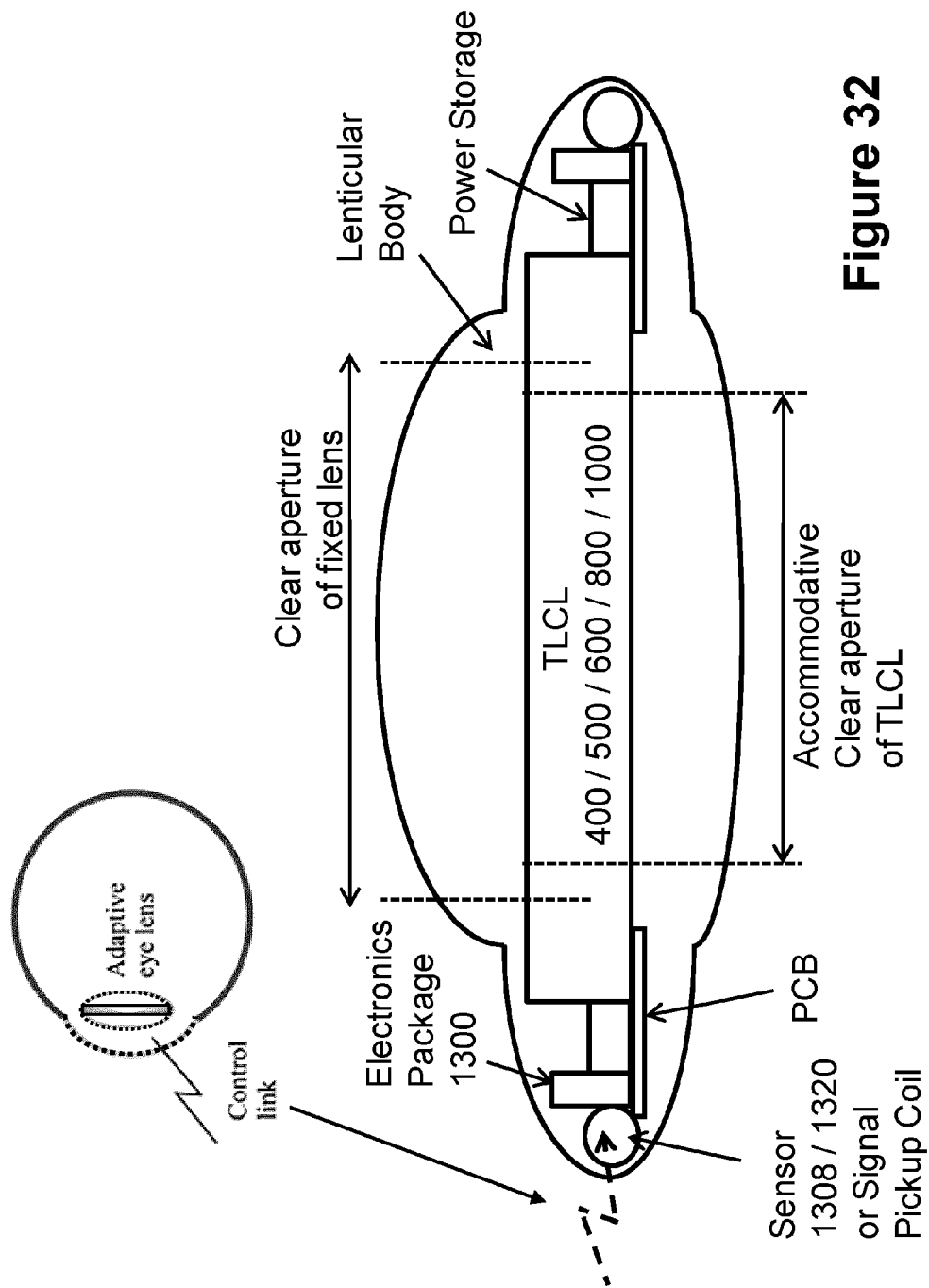
FIG. 32 is a schematic diagram illustrating a tunable liquid crystal lens being used in an intraocular prosthesis in accordance with the proposed solution, wherein similar features bear similar labels throughout the drawings. Reference to "top" and "bottom" qualifiers in the present specification is made solely with reference to the orientation of the drawings as presented in the application and do not imply any absolute spatial orientation.

The above mentioned improved parameters, including but not limited to, increased aperture, increased clear aperture, reduction in image splitting, increase in optical power, reductions in peripheral aberrations, control of aberrations, etc. are beneficial in implementing a tunable LC lens optical device in an intraocular prosthesis for example as illustrated in FIG. 32.

In accordance with some embodiments of the proposed solution, an integral intraocular prosthesis includes a TLCL 400/500/600/800/1000, an electronics package 1300, and power storage on a flexible Printed Circuit Board (PCB), for example made of (biocompatible) Kapton™ (Kapton is a trademark of E. I. du Pont de Nemours and Company or its affiliates), the flexible PCB itself having an aperture. An example of such an integral intraocular prosthesis is illustrated in FIG. 32 to include encapsulating material forming a pronounced fixed optical power element over the TLCL and also encapsulating the electronics package 1300, and power storage. It is understood that FIG. 32 is highly schematic, the lobed shape provides high optical power fixed optical lens elements by employing pronounced lenticular shapes while the power source and electronics package 1300 is disposed around the periphery of the intraocular prosthesis.

FIG. 32 also illustrates in the inset the intraocular prosthesis implanted. Inductive drive coupling may be employed with the TLCL connected as a capacitor in an LRC resonant circuit to charge the intraocular prosthesis in situ. It is understood that while FIG. 32 is highly schematic, an inductive signal pickup coil 1320 need not be a component separate from the intraocular prosthesis and the fixed optical elements need not extend to the edges of the intraocular prosthesis, however TLCL edges contain electrode layer contacts and require encapsulation. It is understood that such a signal receiver element 1320 can also be used as a receiver element of a power coupler to recharge the power storage of such an integral intraocular prosthesis or retard its depletion. For example, an eye glasses frame or an eye patch can be employed (not shown) to recharge the power store (battery or capacitor) either during operation or at night. Such eye glasses frame or eye patch includes an external transmit element for transmitting power.

Further details of an intraocular prosthesis are described in U.S. patent application Ser. No. 13/369,806 filed 2012 Feb. 9 which claims priority from U.S. Provisional Patent Application 61/441,863 filed 2011 Feb. 11, the entireties of which are incorporated herein by reference.

While not shown in the above geometries, an additional transparent conductive layer can be used on a side of the WCL 219 opposite from transparent electrode 212 in order to reorient LC molecular directors away from a disclination zone prior to operating the TLCL.

While reference has been made above to transparent electrodes, either electrically floating or electrically driven, it is understood that such transparent electrodes can have different indices of refraction compared to indices of refraction of immediately adjacent layers such as substrates, alignment layers, weakly conductive layers, etc. It is understood that despite not being shown in the accompanying diagrams, index matching layers may be required between the illustrated layers in order to limit reflections and therefore reduce aberrations.

The liquid crystal cells described above and illustrated in the drawings relate to lenses (and beam steering devices), but other optical devices can also be made using the proposed solution. For example, the liquid crystal material can be mixed with a material having a large anisotropy of absorption (otherwise called "dichroic absorbing" materials) to be controllably oriented to act as a polarization-independent shutter or as a diaphragm device. Differences in absorption coefficients between two orientation states (with respect to the polarization of light) can be some orders of magnitude for well suited material properties; typically the molecule length (namely the aspect ratio) as well its ability to absorb light within the desired spectrum. Carbon nanotubes, chains of dichroic dyes, metal or semiconductor nanorods can offer the aspect ratio, absorption properties and stability suitable for such applications.

While some of the liquid crystal cells described above, and illustrated in the drawings, have a single orientation with two cells of orthogonal orientation for polarization independent operation, it will be appreciated that other arrangements are possible. For example, to provide for better angular independence of operation, multiple cells can provide opposed orientation for each polarization. An example of this is a split-cell design illustrated in FIG. 13A of commonly assigned International Patent Application PCT/CA2009/000743, the specification of which is incorporated herein by reference.

Those skilled in the art will recognize that the various principles and embodiments described herein may also be mixed and matched to create a TLC lens optical devices with various auto-focus characteristics. Electrodes of different shapes and configurations; frequency dependent materials of different types, shapes and positions; dual frequency liquid crystal materials of different types; different drive signal generators; etc. can be used in combination to create a TLC lens optical device with a particular characteristic. The TLC lens devices may be frequency controlled, voltage controlled, or controlled by a combination of the two.

The optical devices illustrated herein can be employed, either in single polarization and/or polarization independent geometry in applications, such as but not limited to: miniature cameras (mobile, cell phone, webcam, tablet, etc.), endoscopic optical elements, corrective lens elements, intraocular devices, Digital Video Disc (DVD)/Blu-Ray™ pick-up systems, etc. ("Blu-Ray" is a trademark of Blu-ray Disc Association).

While the invention has been shown and described with reference to preferred embodiments thereof, it will be recognized by those skilled in the art that various changes in form and detail may be made therein without departing from the spirit and scope of the invention as defined by the appended claims.

The invention claimed is:

1. A liquid crystal gradient index optical device, the optical device comprising:
   a first optical component having an optical aperture within a first aperture and an optical peripheral aberration near a peripheral portion of the first aperture, and
   a second optical component configured to correct the optical peripheral aberration, at least the second optical component comprising:
   at least two substrates;
   an internal tape hole patterned control electrode provided on one of said substrates within said first aperture, said internal control electrode and an external hole patterned control electrode being separated by a gap, said gap forming part of said optical aperture;
   a weakly conductive material provided in association with the internal hole patterned control electrode;
   a planar transparent electrode provided on another of said substrates; and
   an alignment surface provided on said substrates in contact with a layer of liquid crystal material between said substrates,
   wherein an electric field provided by the internal hole patterned control electrode and the planar transparent electrode allow for the liquid crystal material to correct said optical peripheral aberration.

2. The optical device as defined in claim 1, wherein the first optical component comprises:
   said external hole patterned control electrode having a physical aperture corresponding to the first aperture of the first optical component, the external hole patterned control electrode and the internal hole patterned control electrode both interacting with the weakly conductive material,
   wherein electrical signals applied to both of the external hole patterned control electrode and the internal hole patterned control electrode allow for optical quality of the optical device to be controlled predominantly in said gap portion of said optical aperture.

3. The optical device as defined in claim 2, further comprising:
   a floating transparent electrode provided on a side of said one of said substrates opposite said external and said internal hole patterned electrode.

4. The optical device as defined in claim 2, comprising at least three said substrates and two layers of liquid crystal materials, said layers being arranged orthogonally to one another so as to act on both linear polarizations of light.

5. The optical device as defined in claim 4, wherein the external hole patterned control electrode and the internal hole patterned control electrode are located between said two liquid crystal layers and provide electric fields for said two liquid crystal layers.

6. The optical device as defined in claim 4, wherein the external hole patterned control electrode and the internal hole patterned control electrode comprise two external hole patterned control electrodes and two internal hole patterned control electrodes for separately providing electric fields on said two liquid crystal layers.

7. The optical device as defined in claim 4, comprising at least five said substrates and four layers of liquid crystal material, said layers being arranged orthogonally and opposed to one another so as to act on both linear polarizations of light with reduced angular sensitivity.

8. The optical device as defined in claim 2, wherein at least said inner hole patterned electrode comprises a plurality of individually connected segments.

9. The optical device as defined in claim 2, wherein said electrodes are arranged on an inside side of said substrates with respect to said liquid crystal layer.

10. The optical device as defined in claim 2, further comprising a drive circuit configured to drive the external hole patterned electrode and the inner hole patterned electrode separately to provide variable control of an optical property of the device.

11. The optical device as defined in claim 2, wherein the external hole patterned electrode and the inner hole patterned electrode have a circular geometry, and the optical device is a circular lens.

12. The optical device as defined in claim 11, wherein the optical device is an ophthalmic lens.

13. The optical device as defined in claim 11, wherein said first aperture is greater than 4 mm.

14. The optical device as defined in claim 12, wherein the external hole patterned electrode and the inner hole patterned electrode are transparent electrodes, the device having a clear, fixed zero or non-zero optical power ring portion surrounding said aperture.

15. The optical device as defined in claim 12, wherein the device is an implantable, intraocular lens.

16. The optical device as defined in claim 3, wherein said floating transparent electrode is provided over only a central portion of said first aperture.

17. The optical device as defined in claim 16, wherein said floating transparent electrode is provided over said central portion of said first aperture located further from the planar electrode than the inner hole patterned control electrode is located from the planar electrode.

18. The optical device as defined in claim 8, wherein both said external hole patterned electrode and said inner hole patterned electrode, comprise a corresponding plurality of individually connected segments.

19. The optical device as defined in claim 13, wherein said first aperture is greater than 5 mm.

20. The optical device as defined in claim 19, wherein said first aperture is greater than 6 mm.

\* \* \* \* \*